(12) United States Patent
Lonsinger et al.

(10) Patent No.: US 12,064,241 B2
(45) Date of Patent: *Aug. 20, 2024

(54) HINGED PROBE COVER FOR A HANDHELD OXIMETRY PROBE

(71) Applicant: ViOptix, Inc., Newark, CA (US)

(72) Inventors: Mark Lonsinger, San Jose, CA (US); Scott E. Coleridge, New York, NY (US); Kate LeeAnn Bechtel, Pleasant Hill, CA (US); William Welch, Sunnyvale, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/172,247

(22) Filed: Feb. 21, 2023

(65) Prior Publication Data

US 2023/0190153 A1 Jun. 22, 2023

Related U.S. Application Data

(63) Continuation of application No. 16/941,480, filed on Jul. 28, 2020, now Pat. No. 11,583,211, which is a (Continued)

(51) Int. Cl.
*A61B 5/1455* (2006.01)
*A61B 5/00* (2006.01)
*A61B 5/107* (2006.01)

(52) U.S. Cl.
CPC ........ *A61B 5/14551* (2013.01); *A61B 5/1075* (2013.01); *A61B 5/14552* (2013.01);
(Continued)

(58) Field of Classification Search
CPC . A61B 5/0205; A61B 5/1455; A61B 5/14551; A61B 5/14552; A61B 5/14532;
(Continued)

(56) References Cited

U.S. PATENT DOCUMENTS

| 5,619,992 A | 4/1997 | Guthrie et al. |
| 5,827,182 A | 10/1998 | Raley et al. |
| | (Continued) | |

FOREIGN PATENT DOCUMENTS

| EP | 0102816 A2 | 3/1984 |
| EP | 1889569 B1 | 6/2014 |
| | (Continued) | |

OTHER PUBLICATIONS

International Search Report, PCT Application PCT/US2017/028700, Aug. 2, 2017, 6 pages.
(Continued)

*Primary Examiner* — Chu Chuan Liu

(74) *Attorney, Agent, or Firm* — Aka Chan LLP

(57) ABSTRACT

A sleeve or sheath includes a body having a top opening. The body covers a handheld oximeter probe or a portion of the probe. The sleeve has a shape that approximately matches the oximeter probe or portion of the probe, which is covered by the sleeve. The sleeve has a top opening that allows a user to slide the oximeter probe into the sleeve. The sleeve is transparent to radiation emitted and collected by the oximeter probe. The sleeve is formed of a material that prevents patient tissue, fluid, viruses, bacteria, and fungus from contacting the covered portions of the oximeter probe. The sleeve leaves the probe relatively sterile after use so that little or no clearing of the probe is required for a subsequent use, such as when the probe is covered with a new, unused sleeve.

22 Claims, 13 Drawing Sheets

Related U.S. Application Data continuation of application No. 15/493,121, filed on Apr. 20, 2017, now Pat. No. 10,722,156.

(60) Provisional application No. 62/363,562, filed on Jul. 18, 2016, provisional application No. 62/326,630, filed on Apr. 22, 2016, provisional application No. 62/326,673, filed on Apr. 22, 2016, provisional application No. 62/326,644, filed on Apr. 22, 2016, provisional application No. 62/325,919, filed on Apr. 21, 2016, provisional application No. 62/325,413, filed on Apr. 20, 2016, provisional application No. 62/325,403, filed on Apr. 20, 2016, provisional application No. 62/325,416, filed on Apr. 20, 2016.

(52) U.S. Cl.
CPC .......... *A61B 5/6887* (2013.01); *A61B 5/7235* (2013.01); *A61B 2560/0214* (2013.01); *A61B 2560/0425* (2013.01); *A61B 2562/242* (2013.01); *A61B 2562/247* (2013.01)

(58) Field of Classification Search
CPC ...... A61B 2560/0425; A61B 2562/242; A61B 2562/247
See application file for complete search history.

(56) References Cited

U.S. PATENT DOCUMENTS

| | | |
|---|---|---|
| 6,385,821 B1 | 5/2002 | Modgil et al. |
| 7,236,813 B2 | 6/2007 | Parker |
| 8,233,955 B2 | 7/2012 | Al-ali et al. |
| 8,938,279 B1 | 1/2015 | Heaton, II et al. |
| 2003/0009092 A1 | 1/2003 | Parker |
| 2004/0034294 A1 | 2/2004 | Kimball et al. |
| 2005/0209516 A1 | 9/2005 | Fraden |
| 2006/0053522 A1 | 3/2006 | Kimbell |
| 2006/0169607 A1* | 8/2006 | Carnevali ............ G06F 1/1626 206/320 |
| 2007/0038043 A1 | 2/2007 | Gelikonov et al. |
| 2007/0244377 A1 | 10/2007 | Cozad et al. |
| 2008/0319290 A1 | 12/2008 | Mao et al. |
| 2009/0203998 A1* | 8/2009 | Klinghult ............ A61B 5/6887 600/443 |
| 2009/0253968 A1 | 10/2009 | Cho et al. |
| 2010/0005630 A1 | 1/2010 | Gitman et al. |
| 2010/0292549 A1 | 11/2010 | Shuler |
| 2010/0298728 A1 | 11/2010 | Addison et al. |
| 2011/0028814 A1 | 2/2011 | Petersen et al. |
| 2011/0205535 A1 | 8/2011 | Soller et al. |
| 2011/0224518 A1 | 9/2011 | Tindi et al. |
| 2011/0276276 A1 | 11/2011 | Kashyap et al. |
| 2012/0289801 A1 | 11/2012 | Yamaguchi |
| 2012/0330126 A1 | 12/2012 | Hoppe et al. |
| 2013/0023743 A1 | 1/2013 | Al-ali et al. |
| 2013/0150729 A1 | 6/2013 | Zuluage |
| 2013/0317331 A1 | 11/2013 | Bechtel et al. |
| 2014/0046152 A1 | 2/2014 | Bechtel et al. |
| 2014/0180043 A1 | 6/2014 | Addison et al. |
| 2014/0288386 A1 | 9/2014 | Zand et al. |
| 2016/0000508 A1 | 1/2016 | Finn |

FOREIGN PATENT DOCUMENTS

| | | |
|---|---|---|
| WO | 2009090665 A1 | 7/2009 |
| WO | 2010011763 | 1/2010 |
| WO | 2010042264 A1 | 4/2010 |
| WO | 2013166461 A1 | 11/2013 |
| WO | 2014026200 | 2/2014 |

OTHER PUBLICATIONS

European Patent Office, Extended European Search Report, EP Application No. 17786666.2, Nov. 19, 2019, 2 pages.

* cited by examiner

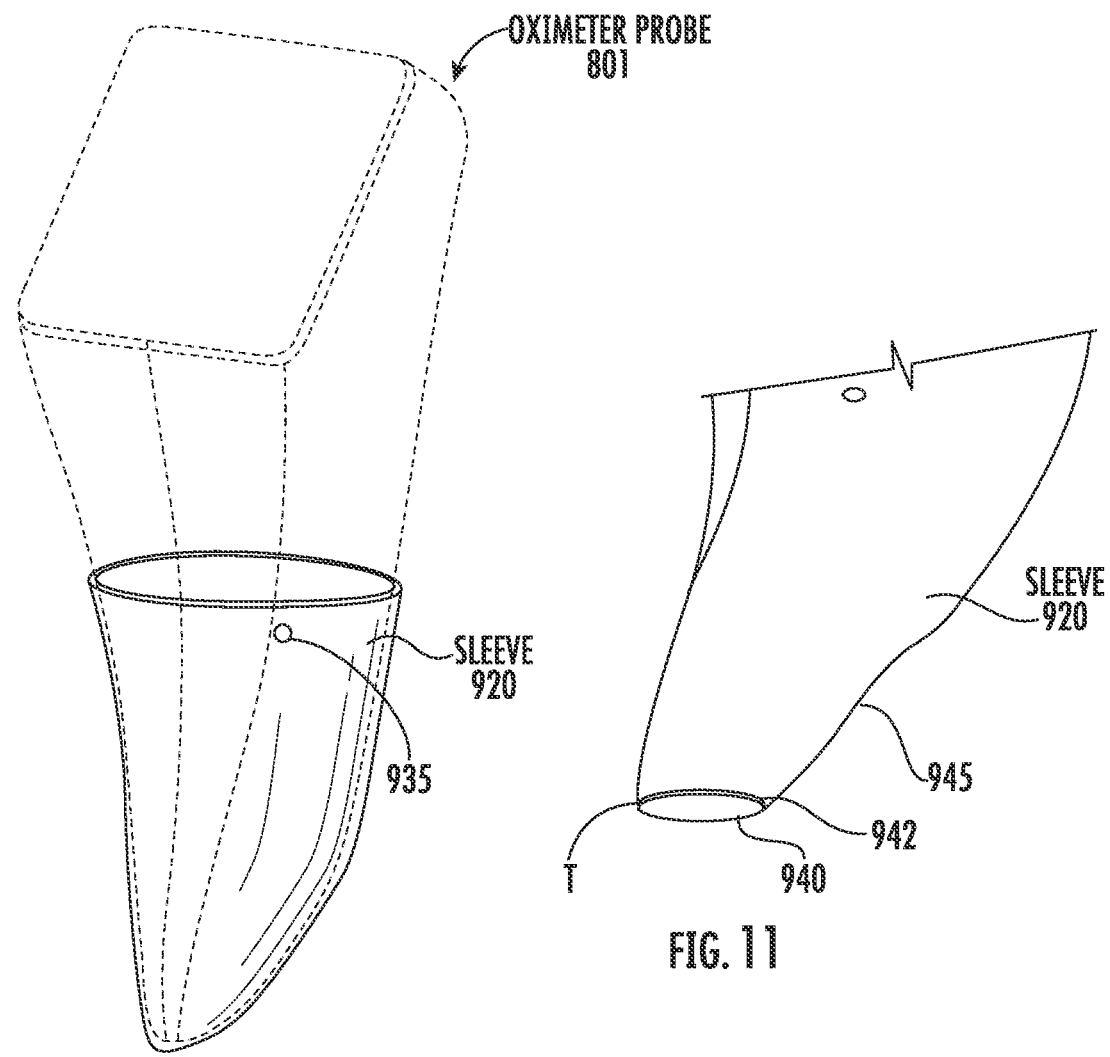

HINGED PROBE COVER FOR A HANDHELD OXIMETRY PROBE

CROSS-REFERENCE TO RELATED APPLICATIONS

This patent application is a continuation of U.S. patent application Ser. No. 16/941,480, filed Jul. 28, 2020, issued as U.S. Pat. No. 11,583,211 on Feb. 21, 2023, which is a continuation of U.S. patent application Ser. No. 15/493,121, filed Apr. 20, 2017, issued as U.S. Pat. No. 10,722,156 on Jul. 28, 2020, which claims the benefit of the U.S. patent applications 62/363,562, filed Jul. 18, 2016; 62/326,630, 62/326,644, and 62/326,673, filed Apr. 22, 2016; 62/325,919, filed Apr. 21, 2016; and 62/325,403, 62/325,413, and 62/325,416, filed Apr. 20, 2016. These applications are incorporated by reference along with all other references cited in these applications.

BACKGROUND OF THE INVENTION

The present invention relates to a sleeve that covers a handheld oximeter probe while the oximeter probe is in use. The sleeve prevents the oximeter probe from becoming contaminated with patient tissue or fluid during use and facilitates the reuse of the oximeter probe or a portion of the oximeter probe.

Oximeters are medical devices used to measure oxygen saturation of tissue in humans and living things for various purposes. For example, oximeters are used for medical and diagnostic purposes in hospitals and other medical facilities (e.g., operating rooms for surgery, recovery room for patient monitoring, or ambulance or other mobile monitoring for, e.g., hypoxia); sports and athletic purposes at a sports arena (e.g., professional athlete monitoring); personal or at-home monitoring of individuals (e.g., general health monitoring, or person training, such as for a marathon); and veterinary purposes (e.g., animal monitoring). In these environments, oximeters can become contaminated from coming in contact with patient tissue and fluid.

Oximeters tend to be relatively costly devices where reuse of the oximeters or portions of the oximeters can provide a cost saving for medical facilities or others that use these devices. Despite the success of existing oximeters, there is a continuing desire to improve oximeters by providing oximeters that can be reused.

Therefore, there is a need for improved oximeters and sleeves that cover the oximeters during use and that facilitate reuse of all or a portion of the oximeters.

BRIEF SUMMARY OF THE INVENTION

A sleeve for a handheld oximeter probe is provided that prevents patient tissue and fluid from penetrating the sleeve and contacting the covered portion of the oximeter probe. The sleeve also prevents prions, viruses, bacteria, fungus, and other biological contaminants from penetrating the sleeve and contacting the covered portion of the oximeter probe. Thereby, the oximeter probe or the portion of the oximeter probe can be kept generally clean (e.g., hygienic), sterile, or both during use and can be reused.

The material of the sleeve has relatively small pore side to inhibit or prevent various contaminants from passing through the sleeve to contact the oximeter probe in the sleeve. The pores can inhibit blood, blood constituents, water, bacteria, viruses, or prions from penetrating the sleeve.

The sleeve conforms to the shape of the oximeter probe so that the sleeve lays relatively taught to the probe. As such, the sleeve is easy to grip by a user without the oximeter probe moving about inside of the sleeve negatively affecting the grip of the user on the sleeve and the device. The sleeve can include panels that have the general shape of the oximeter probe or can stretch to conform to the shape.

In an implementation, a probe cover or sleeve for a oximeter device includes an open end into which a probe tip of the oximeter device is inserted in the probe cover, wherein the probe tip comprises an optical sensor and an optical interface portion. The optical interface portion is positioned against the optical sensor or the probe tip of the oximeter device when the probe tip is inserted in the probe cover. The probe cover includes a barrier coupled to the optical interface portion. The barrier is a barrier for contaminants on a tissue being measured by the oximeter device from contacting the probe tip while allowing optical energy emitted by the optical sensor to pass through the optical interface portion of the probe cover to the tissue and allowing optical energy reflected by the tissue to pass through the optical interface portion of the probe cover to the optical sensor. The optical interface portion comprises a thickness of less than about 250 microns. A first index of refraction of the optical interface portion differs from a second index of refraction for the optical sensor by less than 50 percent. The optical interface portion is between a first surface and a second surface. The first surface will be positioned against the optical sensor. The second surface will be positioned against the tissue. The first surface and second surfaces are parallel to each other.

In an implementation, a kit includes an oximeter probe comprising: a body portion comprising: a rectangular tubular portion includes a front side surface and a back side surface, coupled together by first and second side surfaces; and a tip portion includes: a first finger rest surface, coupled to the front side surface, wherein the first finger rest surface is a convex surface that extends at a first angle in a first turn direction relative to the front side surface; a front tip surface, coupled to the first finger rest surface, wherein the front tip surface extends at a second angle in a second turn direction relative to the first finger rest surface; a bottom face surface, coupled to the front tip surface, wherein the bottom face surface extends at a third angle in the second turn direction relative to the first finger rest surface, and the bottom face surface includes an opening which will retain a sensor head of the device; a second finger rest finger, coupled to the back side surface, wherein the second finger rest surface is a concave surface that extends at a fourth angle in the first turn direction relative to the back side surface; and a back tip surface, coupled between the second finger rest surface and the bottom face surface, wherein the back tip surface is a convex surface that extends at a fifth angle in the first turn direction relative to the second finger rest surface.

The kit includes a probe cover that conforms to a shape of one or more portions of the oximeter probe including an open end into which a probe tip of the oximeter device is inserted in the probe cover, wherein the probe tip includes an optical sensor, and when the probe tip is fully inserted in the probe cover; an optical interface portion, wherein the optical interface portion is positioned against the optical sensor or the probe tip of the oximeter device when the probe tip is in the probe cover; and a barrier coupled to the optical interface portion. The barrier is a barrier for contaminants on a tissue being measured by the oximeter device from contacting the probe tip while allowing optical energy emitted by the optical sensor to pass through the optical interface portion of the probe cover to the tissue and allowing optical energy reflected by the tissue to pass through the optical interface portion of the probe cover to the optical sensor. The optical interface portion has a thickness of less than about 250 microns.

In an implementation, a method includes forming a sleeve, where forming the sleeve includes forming an open end of the sleeve into which a probe tip of the oximeter device is insertable in the probe cover, wherein the probe tip includes an optical sensor; and forming an optical interface portion. The optical interface portion is positioned against the optical sensor or the probe tip of the oximeter device when the probe tip is inserted in the probe cover. Forming the sleeve includes forming a barrier coupled to the optical interface portion. The barrier is a barrier for contaminants on a tissue being measured by the oximeter device from contacting the probe tip while allowing optical energy emitted by the optical sensor to pass through the optical interface portion of the probe cover to the tissue and allowing optical energy reflected by the tissue to pass through the optical interface portion of the probe cover to the optical sensor. Forming the sleeve includes forming the optical interface portion having a thickness of less than about 250 microns; allowing an first index of refraction of the optical interface portion to differ from a second index of refraction for the optical sensor by less than 50 percent; forming the optical interface portion to be between a first surface and a second surface, where the first surface will be positioned against the optical sensor and the second surface will be positioned against the tissue; and forming the first surface and second surfaces are parallel to each other.

In an implementation, a sleeve includes a tubular portion that includes a front side panel, a back side panel, a first side panel, and a second side panel. The front side panel and the back side panel are coupled together by the first and second side panels. The sleeve includes a tip portion that includes a first finger-rest panel coupled to the front side panel; a bottom face panel coupled to the first finger-rest panel; and a second finger-rest panel coupled between the bottom face panel and the back side panel. The bottom face panel has a top surface and a bottom surface that are parallel surfaces. The tubular portion and the first and second finger-rest panels are formed of a first material and the bottom face panel is formed of at least a second material. The sleeve conforms to a shape of an oximeter probe when the oximeter probe is positioned in the sleeve. The bottom face panel is positioned to contact a first surface of a faceplate of the oximeter probe when the oximeter probe is positioned in the sleeve. Top and bottom surfaces of the bottom face panel are parallel with the first surface of the faceplate. The second material has an index of refraction that matches or is similar to an index of refraction of the faceplate where the index of refraction is at or between about 1 and 1.6, between about 1.2 and 1.5, between about 1.3 and 1.5, between about 1.33 and about 1.46. The index of refraction can differ between about 50 percent or less, about 40 percent or less, about 30 percent or less, about 20 percent or less, about 10 percent or less, about 5 percent or less, about 2.5 percent or less, about 1 percent or less, about 0.5 percent or less, the same, or other values. Panels other than the bottom face panels are sometimes referred to as the barrier.

The index of refractions of the faceplate and the other panels of the sleeve can be the same or different. For example, the index of refraction of the faceplate can be higher or lower than the other panels of the sleeve. For example the index of refraction of the panels of the sleeve can be less than about 1.46, less than about 1.4, less than about 1.35, less than about 1.3, less than about 1.25, less than about 1.2, less than about 1.1, or have other values, where an index of refraction of the faceplate can be above the one of these indices of refraction for the other panels.

The bottom face panel is transparent to wavelengths of light at or between about 650 nanometers and about 900 nanometers.

In an implementation, a sleeve device for an oximeter probe includes a rectangular tubular portion comprising a front side panel, a back side panel, a first side panel, and a second side panel, wherein the front side panel and the back side panel are coupled together by the first and second side panels. The tip portion includes a first finger-rest panel coupled to the front side panel. The first finger-rest panel is a convex panel that extends at a first angle in a first turn direction relative to the front side panel. The tip includes a front tip panel that is coupled to the first finger-rest panel. The front tip panel extends at a second angle in a second turn direction relative to the first finger-rest panel. The tip includes a bottom face panel that is coupled to the front tip panel. The bottom face panel extends at a third angle in the second turn direction relative to the first finger-rest panel. The tip includes a second finger-rest panel that is coupled between the bottom face panel and the back side panel. The second finger-rest panel is a concave panel that extends at a fourth angle in the first turn direction relative to the back side panel.

In an implementation, a sleeve device for an oximeter probe includes a tubular portion comprising a front side panel, a back side panel, a first side panel, and a second side panel. The front side panel and the back side panel are coupled together by the first and second side panels, and a first edge of the front side panel, the back side panel, the first side panel, and the second side panel form a first opening. The sleeve device includes a top portion that includes a cover panel coupled to the front side panel via a concave coupling. The cover panel extends at a first angle in a first turn direction relative to the front side panel. The top portion includes a display cover panel coupled to the cover panel via a convex coupling. The display cover panel extends at a second angle in a second turn direction relative to the cover panel. A second edge of the display cover panel, the back side panel, the first side panel, and the second side panel form a second opening that is distally positioned on the sleeve with respect to the first opening.

In an implementation, a sleeve device for an oximeter probe includes a rectangular tubular portion comprising a front side panel, a back side panel, a first side panel, and a second side panel. The front side panel and the back side panel are coupled together by the first and second side panels. The tip portion includes a first finger-rest panel coupled to the front side panel. The first finger-rest panel is a convex panel that extends at a first angle in a first turn direction relative to the front side panel. The tip portion includes a front tip panel that is coupled to the first finger-rest panel. The front tip panel extends at a second angle in a second turn direction relative to the first finger-rest panel. The tip panel includes a bottom face panel that is coupled to the front tip panel. The bottom face panel extends at a third angle in the second turn direction relative to the first finger-rest panel. The tip panel includes a second finger-rest panel that is coupled between the bottom face panel and the back side panel. The second finger-rest panel is a concave panel that extends at a fourth angle in the first turn direction relative to the back side panel.

The sleeve includes a top portion where the top portion includes a cover panel coupled to the front side panel via a concave coupling. The cover panel extends at a fifth angle in the first turn direction relative to the front side panel. The top portion includes a display cover panel that is coupled to the cover panel via a convex coupling. The display cover panel extends at a sixth angle in the second turn direction relative to the cover panel. An edge of the display cover panel, the back side panel, the first side panel, and the second side panel form an opening, such that an oximeter probe can be accepted into the opening.

A kit implementation includes an oximeter probe and a sleeve that is adapted for covering a portion of the oximeter probe. The sleeve includes a rectangular tubular portion comprising a front side panel, a back side panel, a first side panel, and a second side panel. The front side panel of the sleeve and the back side panel of the sleeve are coupled together by the first and second side panels. A tip portion of the sleeve includes a first finger-rest panel coupled to the front side panel. The first finger-rest panel is a convex panel that extends at a first angle in a first turn direction relative to the front side panel. The tip includes a front tip panel that is coupled to the first finger-rest panel. The front tip panel extends at a second angle in a second turn direction relative to the first finger-rest panel. The tip portion includes a bottom face panel that is coupled to the front tip panel. The bottom face panel extends at a third angle in the second turn direction relative to the first finger-rest panel. The tip portion includes a second finger-rest panel that is coupled between the bottom face panel and the back side panel. The second finger-rest panel is a concave panel that extends at a fourth angle in the first turn direction relative to the back side panel. The kit includes a user manual for operating the oximeter probe and a user manual for operating the sleeve. The kit can include a battery for powering the oximeter probe. The kit can also include one or more "fast" cards that have abbreviated instructions for operating the oximeter probe or the sleeve where the abbreviated instructions are an abbreviation of the instruction in the instruction manuals.

Other objects, features, and advantages of the present invention will become apparent upon consideration of the following detailed description and the accompanying drawings, in which like reference designations represent like features throughout the figures.

BRIEF DESCRIPTION OF THE DRAWINGS

FIG. 10 shows a sleeve in an implementation.

FIG. 11 shows a perspective view of the bottom of the sleeve.

DETAILED DESCRIPTION OF THE INVENTION

The present invention generally relates to sleeves or sheaths that cover oximeter probes or portions of oximeter probes so that the oximeter probes or portions can be reused. A sleeve acts a barrier during use for hygiene and sterility (e.g., preventing the spread of germs), while still allowing full functionality of the oximeter probe (e.g., optically transparent). The sleeve keeps patient tissue and fluid from contacting the portion of the oximeter probe covered by the sleeve. The sleeve also prevents one or more of prions, viruses, bacteria, fungus, and other biological contaminants from contacting the oximeter probe or portion. Thereby, the sleeve facilitates reuse of the oximeter probe or portion rather than disposing of the oximeter probe or portion after use.

Figure 1:
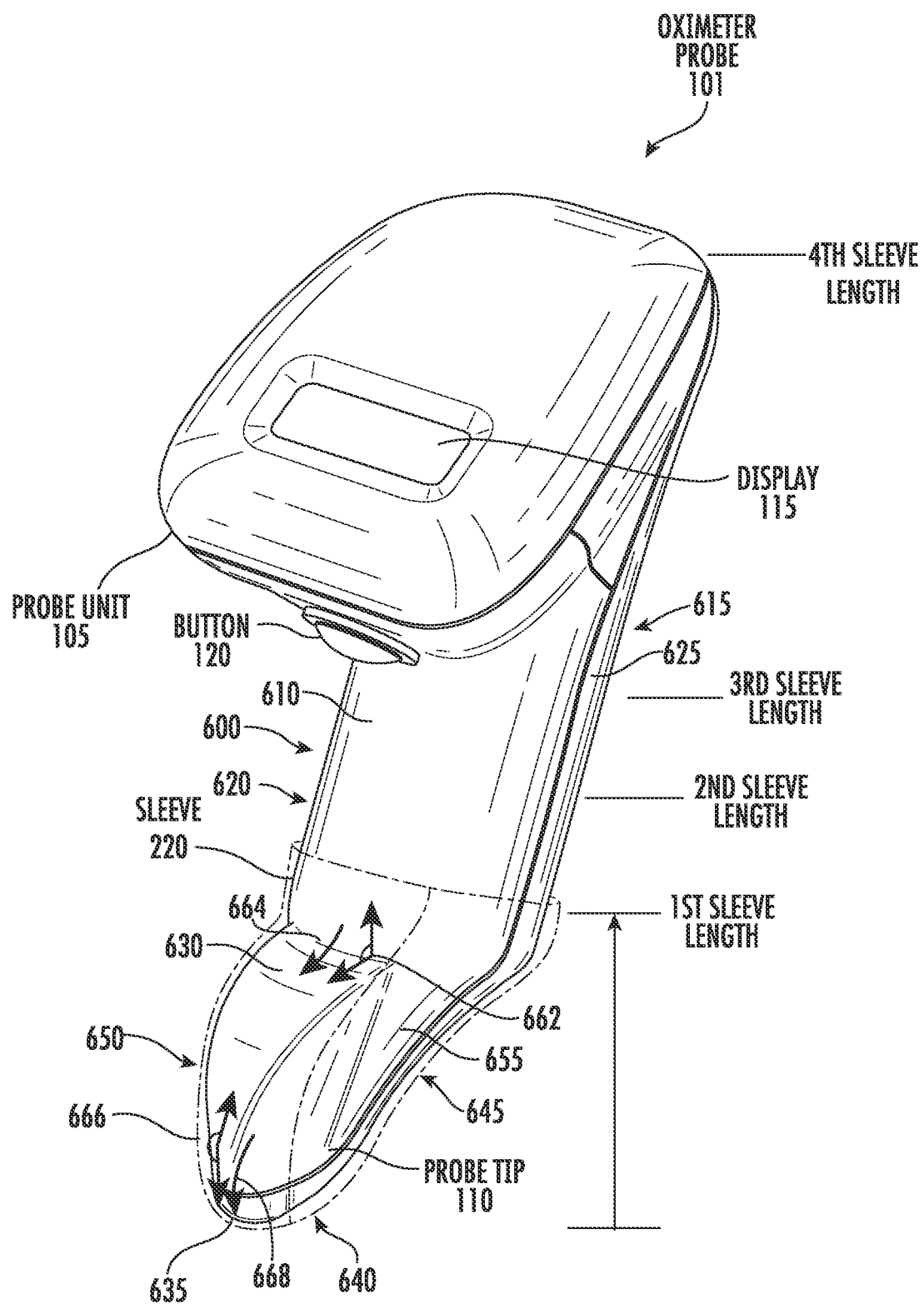
FIG. 1 shows a probe tip of an oximeter probe covered by a sleeve in an implementation.

FIG. 1 shows an oximeter probe 101. This oximeter probe is used to make oxygen saturation measurement of target tissue. In an implementation, the oximeter probe is a tissue oximeter, but in other implementations, the oximeter probe is a pulse oximeter.

Oximeter probe 101 has two portions, a probe unit 105 and a probe tip 110. The probe unit forms an upper portion of the oximeter probe and the probe tip forms a lower portion of the oximeter probe. In an implementation, the probe tip is detachable by a user from the probe unit and can be replaced by the user with a different probe tip. When the probe unit and probe tip are attached together, the oximeter probe operates as a standalone handheld oximeter, without the need to be attached by cabling to another unit. In some implementations, the probe tip is not detachable from the probe unit.

The oximeter probe has a display 115 (e.g., an LCD display, such as a touch LED display) and a button 120. When the button is depressed, light, infrared radiation (IR), or both is emitted at the probe tip into a target tissue to be measured, and reflected light or IR from the target tissue is received at the probe tip. From the received light or IR, the oximeter probe determines a measured oxygen saturation for the tissue. An indicator (e.g., a numerical value or a graphical indicator) for the measured oxygen saturation is displayed on the display.

The following patent applications describe various oximeter devices and oximetry operation, and discussion in the following applications can be combined with aspects of the invention described in this application, in any combination. The following patent application are incorporated by reference along with all references cited in these application Ser. No. 14/944,139, filed Nov. 17, 2015, Ser. No. 13/887,130 filed May 3, 2013, Ser. No. 15/163,565, filed May 24, 2016, Ser. No. 13/887,220, filed May 3, 2013, Ser. No. 15/214,355, filed Jul. 19, 2016, Ser. No. 13/887,213, filed May 3, 2013, Ser. No. 14/977,578, filed Dec. 21, 2015, Ser. No. 13/887, 178, filed Jun. 7, 2013, Ser. No. 15/220,354, filed Jul. 26, 2016, Ser. No. 13/965,156, filed Aug. 12, 2013, Ser. No.

15/359,570, filed Nov. 22, 2016, Ser. No. 13/887,152, filed May 3, 2013, Ser. No. 29/561,749, filed Apr. 16, 2016, 61/642,389, 61/642,393, 61/642,395, 61/642,399 filed May 3, 2012, and 61/682,146, filed Aug. 10, 2012.

This application describes some examples of implementations with specific dimensions, measurements, and values. These are not intended to be exhaustive or to limit the invention to the precise form described.

Some measurements are in millimeters and angles are in degrees and are approximate values. The values can vary due to, for example, measurement or manufacturing tolerances or other factors (e.g., plus or minus 5 percent, plus or minus 10 percent, plus or minus 15 percent, or plus or minus 20 percent). Further, the measurements are for a specific implementation of the device, and other implementations can have different values, such as certain dimensions made longer to accommodate larger hands or devices.

For the specific implementations described, some specific values, ranges of values, and numbers are provided. These values indicate, for example, dimension, angles, ranges, frequencies, wavelengths, numbers, and other quantities (e.g., numbers of sensors, sources, detectors, diodes, fiber optic cables, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given.

FIG. 1 shows a sleeve 220 placed over the probe tip. The sleeve has a closed body and a top that is open. The sleeve covers the probe face (not shown) at the bottom of the probe tip and extends up the length of the probe tip. The body has a shape that complements the portion of the oximeter probe that is covered by the sleeve. The open top receives the oximeter probe into the sleeve. An elastic band (not shown) can be positioned just below the open top for securing the sleeve to the oximeter probe. Other securing devices, such as adhesives, O-rings, or other mechanical devices can be used to secure the sleeve to the oximeter probe.

In an implementation, probe unit 105 has a shaft 600 that extends downward from the bottom of the probe unit to the top of the probe tip 110. Shaft 600 has a generally rectangular cuboid shape, with a front surface 610, a back surface 615 (not shown in the view of FIG. 1, pointed at by the indicator arrow for reference number 615), a first side surfaces 620 (not shown in the view of FIG. 1, pointed at by the indicator arrow for reference number 620), and a second side surface 625 where the first and second side surfaces join the front and back surfaces. The front and back surfaces can be wider than the first and second side surfaces.

Probe tip 110 has a first finger-rest surface (e.g., thumb rest surface) 630, a front tip surface 635, a bottom surface 640 (not shown in the view of FIG. 1, pointed at by the indicator arrow for reference number 640), a second finger-rest surface 645 (not shown in the view of FIG. 1, pointed at by the indicator arrow for reference number 645), a third side surface 650 (not shown in the view of FIG. 1, pointed at by the indicator arrow for reference number 650), and a fourth side surface 655.

The first finger rest 630 has a convex surface and has a concave connection with the front surface 610. The first finger-rest surface extends at a first turn angle 662 in a first turn direction (e.g. clockwise direction of arrow 664) relative to the front side surface as viewed from the second side surface 625 of the shaft 600 and fourth side surface 655 of probe tip 110. The first finger-rest surface can be adapted for a thumb of a user.

The front tip surface 635 extends at a second turn angle 666 in a second turn direction (e.g. clockwise direction of arrow 668) relative to the first finger-rest surface 630 as viewed from the second side surface 625 of the shaft 600 and fourth side surface 655 of probe tip 110.

The bottom surface 640 extends at a third turn angle in a second turn direction (e.g. clockwise direction) relative to the front tip surface 635 as viewed from the second side surface 625 of the shaft 600 and fourth side surface 655 of probe tip 110.

The second finger-rest surface 645 is a concave surface and extends at a fourth turn angle in the second turn direction relative to the bottom surface 620 as viewed from the second side surface 625 of the shaft 600 and fourth side surface 655 of probe tip 110. In an implementation, the second finger-rest surface is a flat surface or a convex surface. The concave surface rests on a user's finger (e.g., middle finger) where the user's finger supports the oximeter probe.

The back surface 615 extends at a fifth turn angle in the second turn direction relative to the second finger-rest surface 645 as viewed from the second side surface 625 of the shaft 600 and fourth side surface 655 of probe tip 110.

In various implementations, the backside and bottom face surfaces are relatively flat surfaces that are angled relative to each other in a range from 90 degrees to about 150 degrees. A first height of the first finger position above the bottom face surface is greater than a second height of the second finger position above the bottom face surface. The first turn angle is angled relative to the front side surface in a range from 90 degrees to about 60 degrees.

Figure 2A:
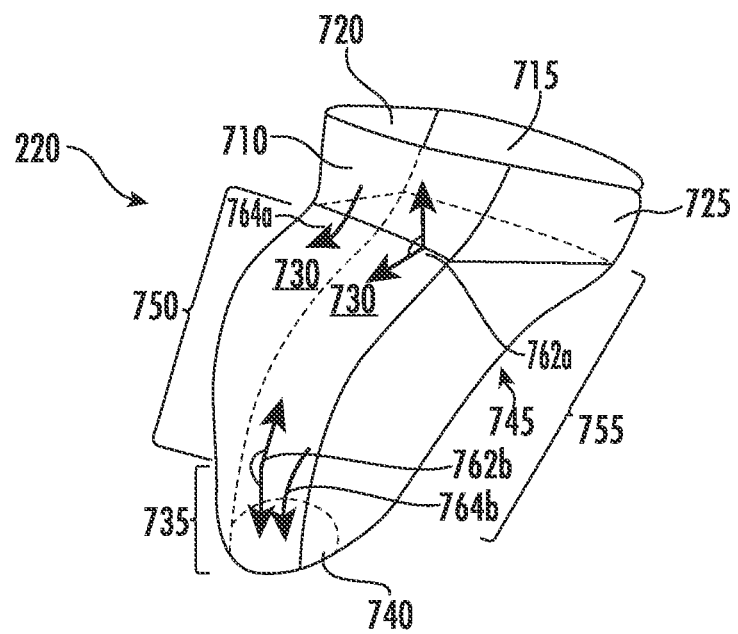
FIGS. 2A-2B show a perspective view and a side view of the sleeve.
Figure 2B:
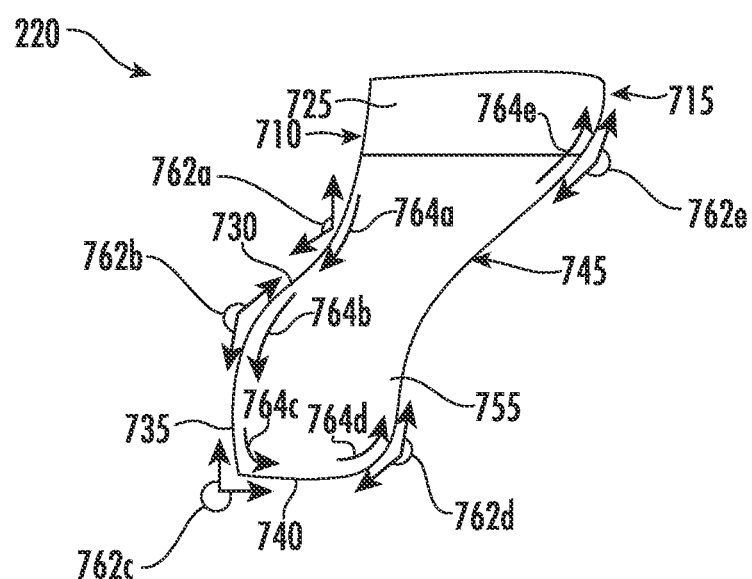

FIGS. 2A-2B show a perspective view and a side view, respectively, of sleeve 220. The broken lines in FIG. 2A represent features of the sleeve that would not be visible in the perspective view of the sleeve shown in this figure.

In an implementation, sleeve 220 has panels that correspond to the above described surfaces of the oximeter probe and has contours and turn angles that correspond to the contours and turn angles of the oximeter probe. Specifically, the sleeve has a front panel 710, a back panel 715, a first upper-side panel 720, a second upper-side panel 725, a first finger panel 730, a front tip panel 735, a bottom panel 740, a second finger-rest panel 745, a first lower-side panel 750, and a second lower-side panel 755. The first upper-side panel and the first lower-side panel are sometimes referred to as a first side panel. The second upper-side panel and the second lower-side panel are sometimes referred to as a second side panel.

The first finger-rest panel 730 has a convex surface and has a concave connection with the front panel 710. The first finger-rest panel extends at a first turn angle 762a in a first turn direction (e.g. clockwise direction of arrow 764a) relative to the front side panel as viewed from the second upper-side panel 725 and second lower-side panel 755. The first finger-rest panel can be adapted to contact a thumb of a user while the first finger-rest surface 630 is supported by the user's thumb.

The front tip panel 735 extends at a second turn angle 762b in a second turn direction (e.g. clockwise direction of arrow 764b) relative to the first finger-rest panel 730 as viewed from the second upper-side panel 725 and second lower-side panel 755.

The bottom panel 740 is a relatively flat panel (e.g., planar) and extends at a third turn angle 762c in the second turn direction (e.g. clockwise direction of arrow 764c) relative to the front tip panel 735 as viewed from the second upper-side panel 725 and second lower-side panel 755.

The bottom panel is adapted to lay relatively flat and planer (e.g., without an air gap) against the probe face of the oximeter probe. The bottom panel can be the same material or a different material from the other panels. The bottom panel can be formed of glass, quartz, polycarbonate, epoxy (e.g., with polished top and bottom surfaces), or other materials. The bottom panel is described further below.

The second finger-rest panel 745 is a concave panel and extends at a fourth turn angle 762d in the second turn direction (e.g., clockwise direction of arrow 764d) relative to the bottom panel 740 as viewed from the second upper-side panel 725 and second lower-side panel 755. The second finger-rest panel can contact a middle finger of a user's hand while the oximeter probe rests on the index finger. A concave second-finger rest panel can have a radius that matches or is compatible with the radius of the second finger-rest surface 645 of the oximeter probe. For example, the radius of curvature of the concave panel can range from 1 centimeters (e.g., relatively highly curved) to about 10 meters (e.g., relatively small curve). Alternatively, the second finger rest panel is flat, convex, or a combination of the described shapes in any combination. The convex panel can have a radius that matches or is compatible with the radius of the second finger-rest surface 645 of the oximeter probe where the second-finger rest surface is convex. For example, the radius of curvature of the convex panel can range from 1 centimeters (e.g., relatively highly curved) to about 10 meters (e.g., relatively small curve).

The back panel 715 extends at a fifth turn angle 762e in the second turn direction (e.g., clockwise direction of arrow 764e) relative to the second finger-rest panel 745 as viewed from the second upper-side panel 725 and second lower-side panel 755.

In an implementation, the top opening can have a diameter or lateral lengths (lengths of each of individual panel 710, 715, 720, and 725) of about 2-10 centimeters. The body of the sleeve can have a range of lengths, such approximately 2 centimeters to 40 centimeters. FIG. 1 shows a number of lengths (e.g., first, second, third, and fourth lengths) of various implementations of the sleeve. For example, the first sleeve length can be about 1.5 centimeters to about 5 centimeters, the second sleeve length can be about 2.5 centimeters to about 20 centimeters, the third sleeve length can be about 3.5 centimeters to about 30 centimeters, and the fourth sleeve length can be about 4.5 centimeters to about 40 centimeters.

These different length sleeves can be used in different use situations, such as dry use environments where fluid is not present and not likely to be splashed onto the oximetry probe, or in wet use environments where the oximeter probe might come in contact with a patient's bodily fluids. A relatively short sleeve may be used in the first use environment whereas a longer sleeve may be used in the latter use environment.

The sleeve is formed of a flexible material, a rubberized material, plastic or a plastic type material, a relatively rigid material or other material that blocks patient tissue and fluid from contacting the portion of the oximeter probe that is covered by the sleeve. The sleeve can also block one or more of prions, viruses, bacteria, fungus, and other contaminants from contacting the portion of the oximeter probe that is covered by the sleeve.

The sleeve can be formed of polycarbonate, latex rubber, polyurethane, polyisoprene, nitrile, silicon, polymer, plastic, cellophane, polyethylene film, combination of ethylene methyl acrylate copolymer and polyethylene film, polyester film, such as Mylar, or other materials that prevents tissue, fluid, prions, viruses, bacteria, fungus, or other contaminants from contacting the covered portion of the oximeter probe. As described above, the bottom panel of the sleeve can be formed of the same or different material as the other panels of the sleeve, such as glass, quartz, polycarbonate, epoxy (e.g., with polished top and bottom surfaces), or other materials. The sleeve or probe cover can include any combination of the materials described. For example, the sleeve can include polycarbonate and polyurethane or polyethylene.

The sleeve can conform to the shape of the oximeter probe. For example, the sleeve can be provided flat, folded, or rolled and opened to receive the oximeter probe. If the sleeve is provided rolled up, the sleeve can unrolled onto the oximeter probe to conform to the probe for use and unrolled or cut from oximeter probe after use. Further, if one or more panels are stretchable, the sleeve can be stretched when the oximeter probe is received in the opening of the sleeve, and the thereafter the one or more panels can contract to conform to the shape of the oximeter probe.

The panels of the sleeve can be formed a continuous material without seams or can be formed of a number of panels that are connected, such as via glue, epoxy, sonic welding, or other connection material and connection technique. The panels can be formed of the same material or different materials.

In an implementation, to block viruses, the sleeve can be formed of a material that has pore sizes of approximately 100 nanometers or less, approximately 50 nanometers or less, approximately 20 nanometers or less; or approximately 15 nanometers or less to block the smallest known viruses. In an implementation, to block proteins, such as prions, the sleeve is formed of a material that has pore sizes of approximately 5-10 nanometers or less. In an implementation, to block fluids, such as water, the sleeve is formed of a material that has pore sizes of approximately 0.30-0.25 nanometers or less.

The sleeve can be used in a variety of environments to protect the oximeter probe or a portion of the probe, such as surgical, sterile environment for spot measurements, doctors offices, at sporting events (e.g., personal and professional sports uses), homes, retirement communities, hospice care, first responders (e.g., paramedics, emergency medical technicians, ambulance care, and fire fighters), pre-operative care, post-operative care, pediatric care, geriatric care, medical rehabilitation centers, veterinary uses, and other users. The use environments for the oximeter probe with the sleeve can range from sterile, to generally sanitary and cleanly environments (e.g., non-sterile recovery rooms in a hospital, doctors offices, and other medical offices, home use, and other environments), and to environments that are typically not sanitary, such as mud, dirt, sand, and dusty environments, snow (e.g., ski areas, ski patrol, and mountain climbing), rain, ice, battle field use, and near bodies of water (e.g., at swimming pools, beaches, and boats). Different sleeve material, such as the sleeve materials described above, can be used for the sleeves for specific sterility uses or specific sanitary uses.

The sleeve can be supplied in a sanitary enclosure that preserves the sterility of the sleeve prior to use. The encloser can be paper, plastic coated paper, plastic, Mylar, or other material.

Figure 3:
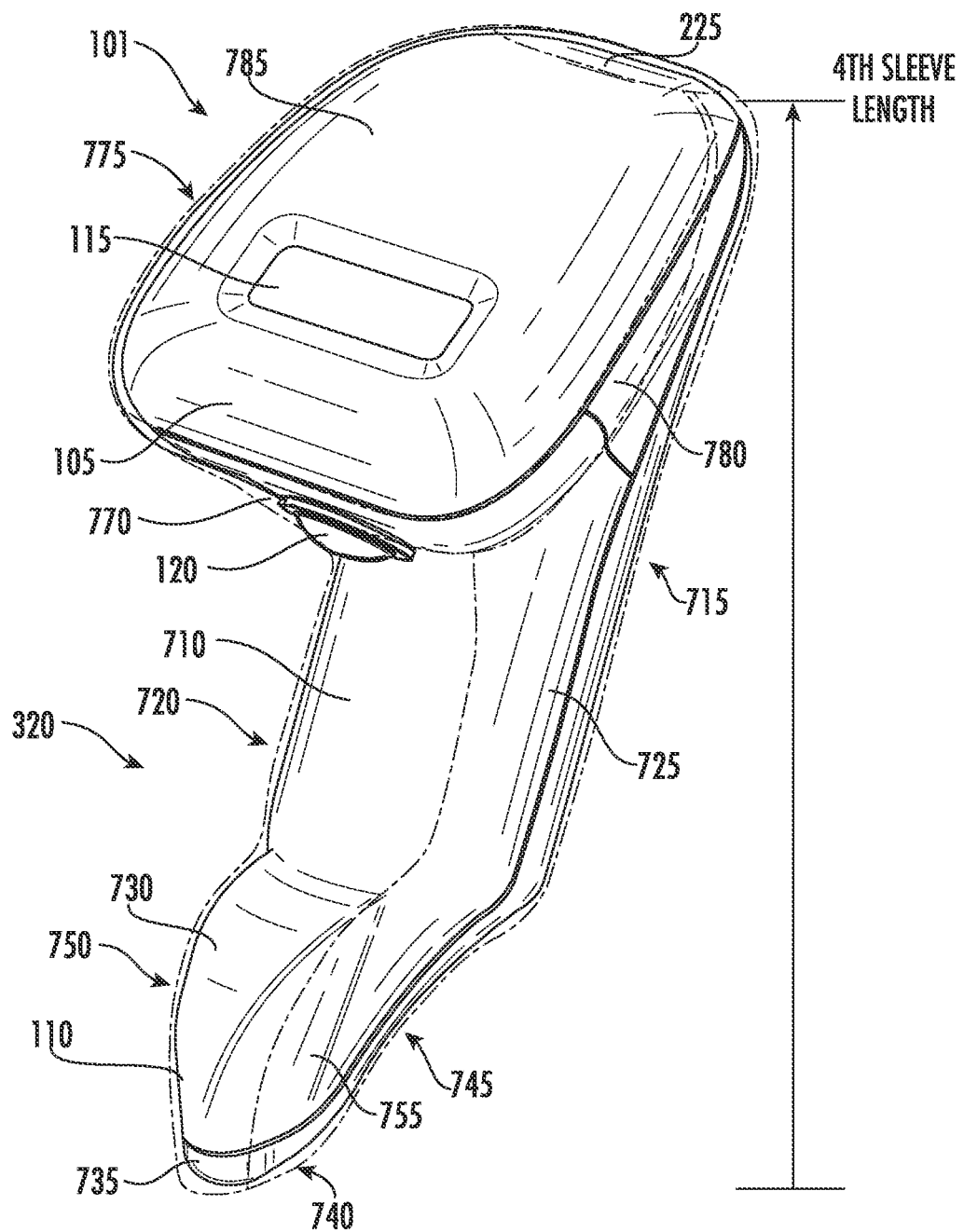
FIG. 3 shows the probe tip and the probe unit of the oximeter probe covered by a sleeve in an implementation.

FIG. 3 shows an implementation of a sleeve 320 having a length that extends to approximately the top of the oximeter probe. The bottom portion of sleeve 320 has the same or similar contours and turn angles as sleeve 220 described above. In addition, sleeve 320 has an extended sleeve portion (e.g., extended sleeve portions of front panel 710, back panel 715, first upper-side panel 720, and second upper-side panel 725) that covers shaft 600.

Sleeve 320 also includes a number of panels that cover all or portions of probe unit 105. Specifically, the sleeve includes a button panel 770, a third side panel 775 (not shown in the view of FIG. 3, pointed at by the indicator arrow for reference number 775), a fourth side panel 780, and a display panel 785. Button panel 770 can be a relatively flat panel or have a contour that accommodates button 120, such as a contour that complements the shape of the button. Button panel 770 has a convex connection with the third side panel 775 and a convex connection with the fourth side panel 780. The button panel, third side panel, and fourth side panel 780 each has a convex connection with the display panel 785.

The third side panel 775 meets the first upper-side panel 720 in a relatively flat connection and the fourth side panel 780 meets the second upper-side panel 725 in a relatively flat connection. Sleeve 320 includes a top opening 225 that opens at the top of the display panel, the tops of the first and second upper-side panels, and at the top of the back panel 715. The opening accepts the oximeter probe into the sleeve.

In an implementation where it is desirable to enclose the entire oximetry probe in the sleeve, the top opening 225 is closable. The top opening can be ringed with an elastic band that closes the top opening after the oximeter probe is place into the sleeve. In an implementation, the sleeve includes an attached flap that can be closed over the top opening. The flap seals the top openings closed. The flap can seal the top opening with an adhesive that can be located on the flap or other part of the sleeve. The adhesive can be protected by a non-stick, pull strip for ease of use.

In an implementation where the sleeve covers the display, at least the display panel of the sleeve is transparent or sufficiently translucent to visible light, such that the display is visible through the sleeve (e.g., at least the display panel of the sleeve) to a user. Further, the sleeve or at least the bottom panel (e.g., faceplate) 740 is transparent to radiation emitted by the oximeter probe into target tissue. For example, the sleeve, the bottom panel, or both are transparent to visible light, IR, or both. For example, the sleeve, the bottom panel, or both can be transparent to light, IR, or both at approximately 760 nanometers and 810 nanometers; approximately 760 nanometers, 810 nanometers, and 850 nanometers; approximately 760 nanometers, 810 nanometers, 850 nanometers, and 900 nanometers; 650 nanometers and about 900 nanometers, about 670 manometers and about 900 nanometers, about 690 nanometers and about 900 nanometers, about 700 nanometers and 900 nanometers, about 710 nanometers and about 900 nanometers, about 720 nanometers and 900 nanometers, 730 nanometers and 900 nanometers, 740 nanometers and 900 nanometers, 750 nanometers and 900 nanometers, 760 nanometers and 900 nanometers, 770 nanometers and 900 nanometers, or other ranges, such as about 650 manometers and about 890 nanometers, about 670 manometers and about 890 nanometers, about 690 nanometers and about 890 nanometers, about 700 nanometers and 890 nanometers, about 710 nanometers and about 890 nanometers, about 720 nanometers and 890 nanometers, 730 nanometers and 890 nanometers, 740 nanometers and 890 nanometers, 750 nanometers and 890 nanometers, 760 nanometers and 890 nanometers, 770 nanometers and 890 nanometers, or other ranges with longest wavelengths less than 890 nanometers. The listed wavelengths and ranges of wavelengths may be transmitted from the oximeter probe and received by the oximeter probe subsequent to transmission through patient tissue. The faceplate can have of transparency of 90 percent or more (e.g., 90 percent or more of incident light passes through the faceplate), 92 percent or more, 94 percent or more, 95 percent or more, 96 percent or more, 97 percent or more, 98 percent or more, 99 percent or more, 99.5 percent or more, or other transparencies. That is the attenuation of the faceplate is 10 percent or less, 8 percent or less, 6 percent or less, 5 percent or less, 4 percent or less, 3 percent or less, 2 percent or less, 1.5 percent or less, 1 percent or less, 0.5 percent or less, or other values.

The faceplate and other panels of the sleeve can have the same or different indices of refraction, and can have the same or different thicknesses. For example, the display panel and the faceplate can have different indices of refraction (e.g., the faceplate can have a higher index of refraction relative to the other panels of the sleeve). The faceplate and other panels of the sleeve can have different thicknesses. For example, the faceplate can be thinner than the other panels of the sleeve by 10 percent, 20 percent, 50 percent, 100 percent, 200 percent, 300 percent, 1000 percent, 2000 percent, or other differences.

Figure 4:
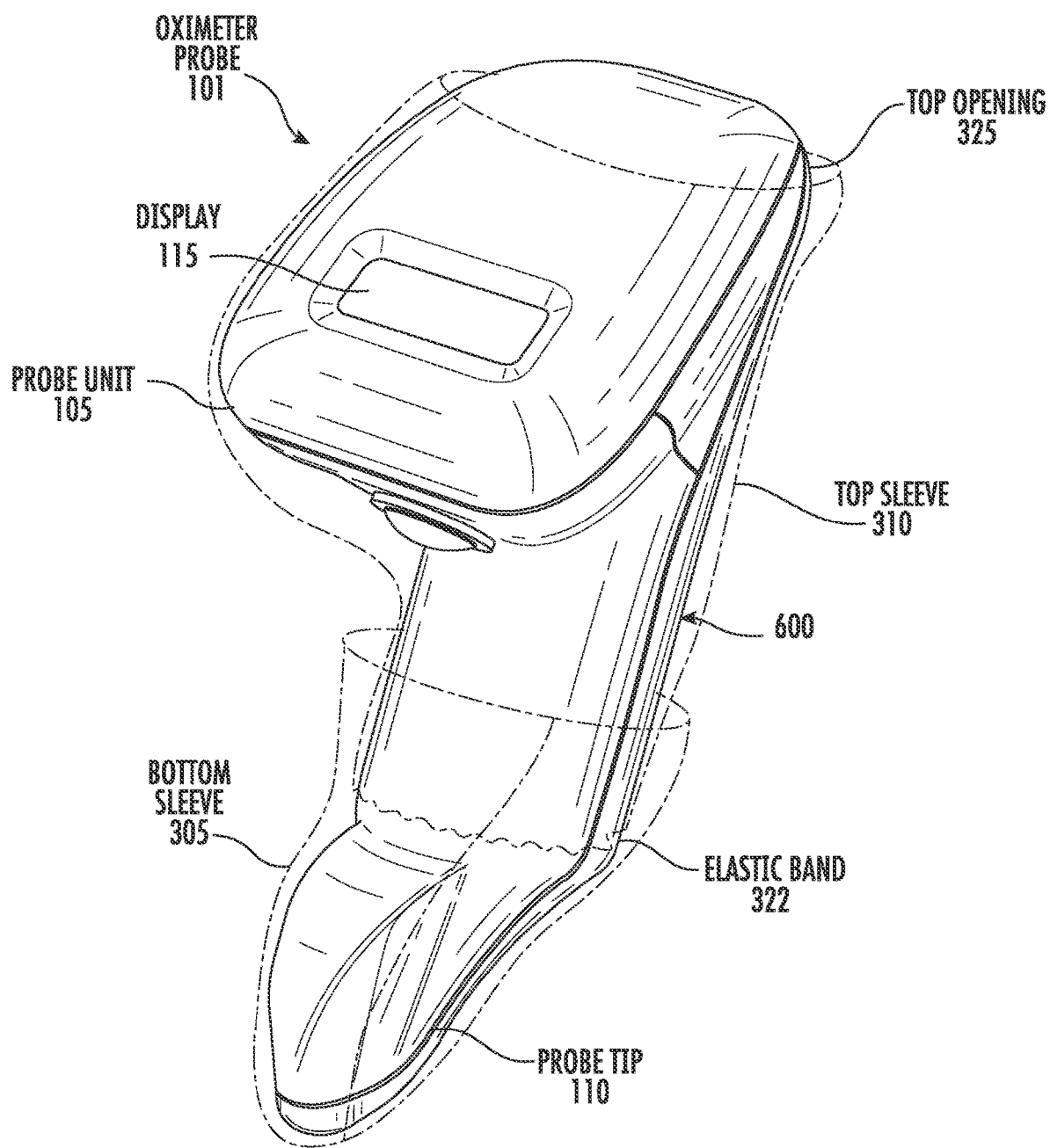
FIG. 4 shows the probe tip and the probe unit of the oximeter probe covered by top and bottom sleeves in an implementation.

FIG. 4 shows an implementation of a bottom sleeve 305 and a top sleeve 310 that overlap along a portion of the oximeter probe. Bottom sleeve 305 covers the probe tip and can cover a portion of the probe unit, such as all or a portion of shaft 600. Bottom sleeve 305 can have the same or similar height (e.g., taller or shorter) as sleeve 220. Top sleeve 310 covers all or a portion of the probe unit 105 and can cover all or a portion of shaft 600. The top sleeve can be the same or similar to a top portion of sleeve 320 shown in FIG. 3 and described above.

One or both of these sleeves can have an elastic band, O-ring, adhesive, or other device that secures the sleeves to the oximeter probe. For example, the top sleeve is shown with an elastic band 322 that secures the top sleeve to the oximeter probe. The top sleeve can include a top opening 325 for sliding the oximeter probe into this sleeve. The overlap of these sleeves allows the oximeter probe to be easily placed into the sleeves, prevents contaminations from reaching the oximeter probe, and facilitates reuse of the oximeter probe.

Figure 5:
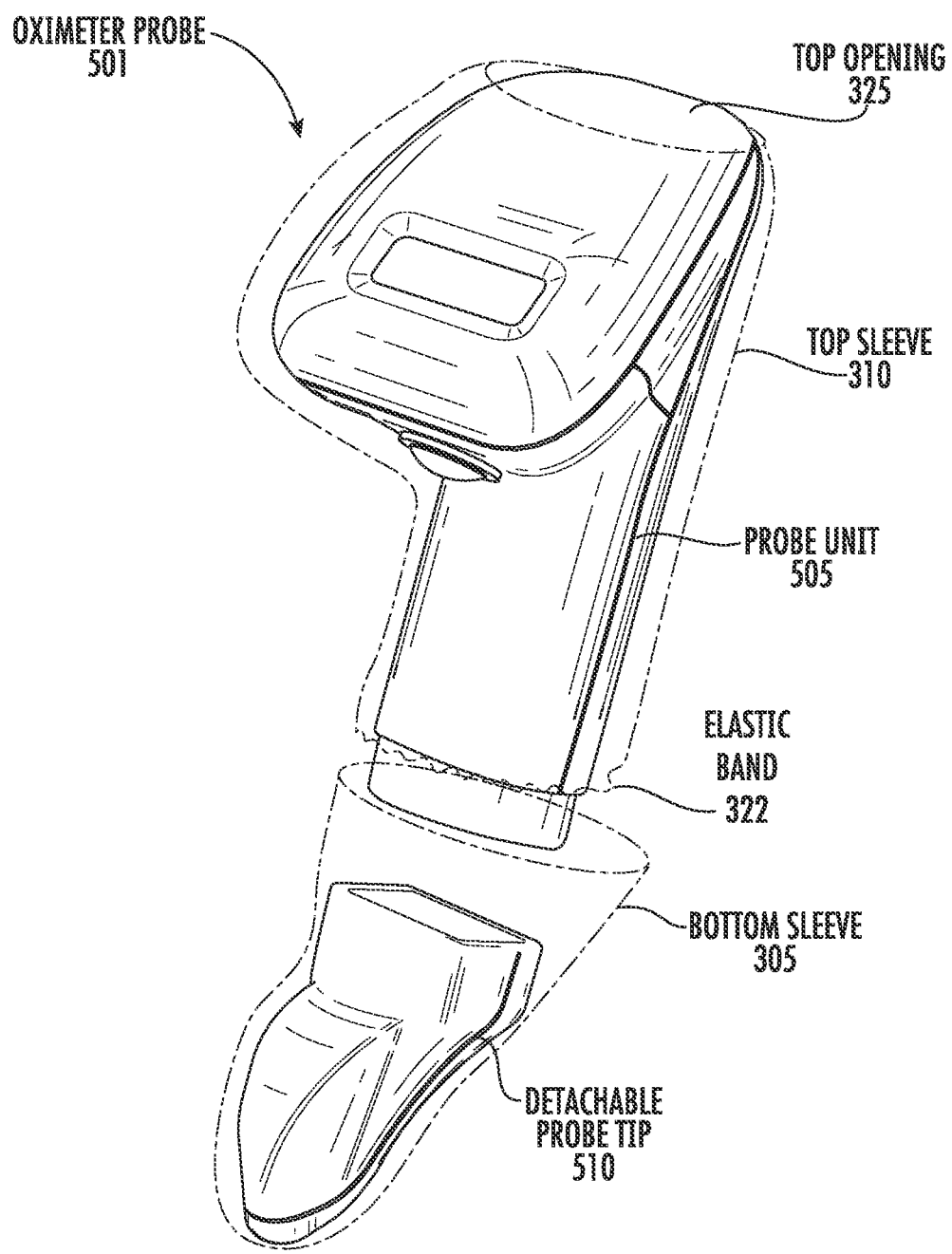
FIG. 5 shows the top and bottom sleeves covering a probe tip and a probe unit of an oximeter probe where the probe tip is attachable to and detachable from the probe unit.

FIG. 5 shows an oximeter probe 501 having two parts. The two parts include a probe unit 505 and a probe tip 510 that is detachable from the probe unit. When attached, the probe unit and probe tip form the working oximeter probe 501. Any of the foregoing described sleeves can be used with oximeter probe 501, such as bottom sleeve 305 and top sleeve 310.

Figure 6:
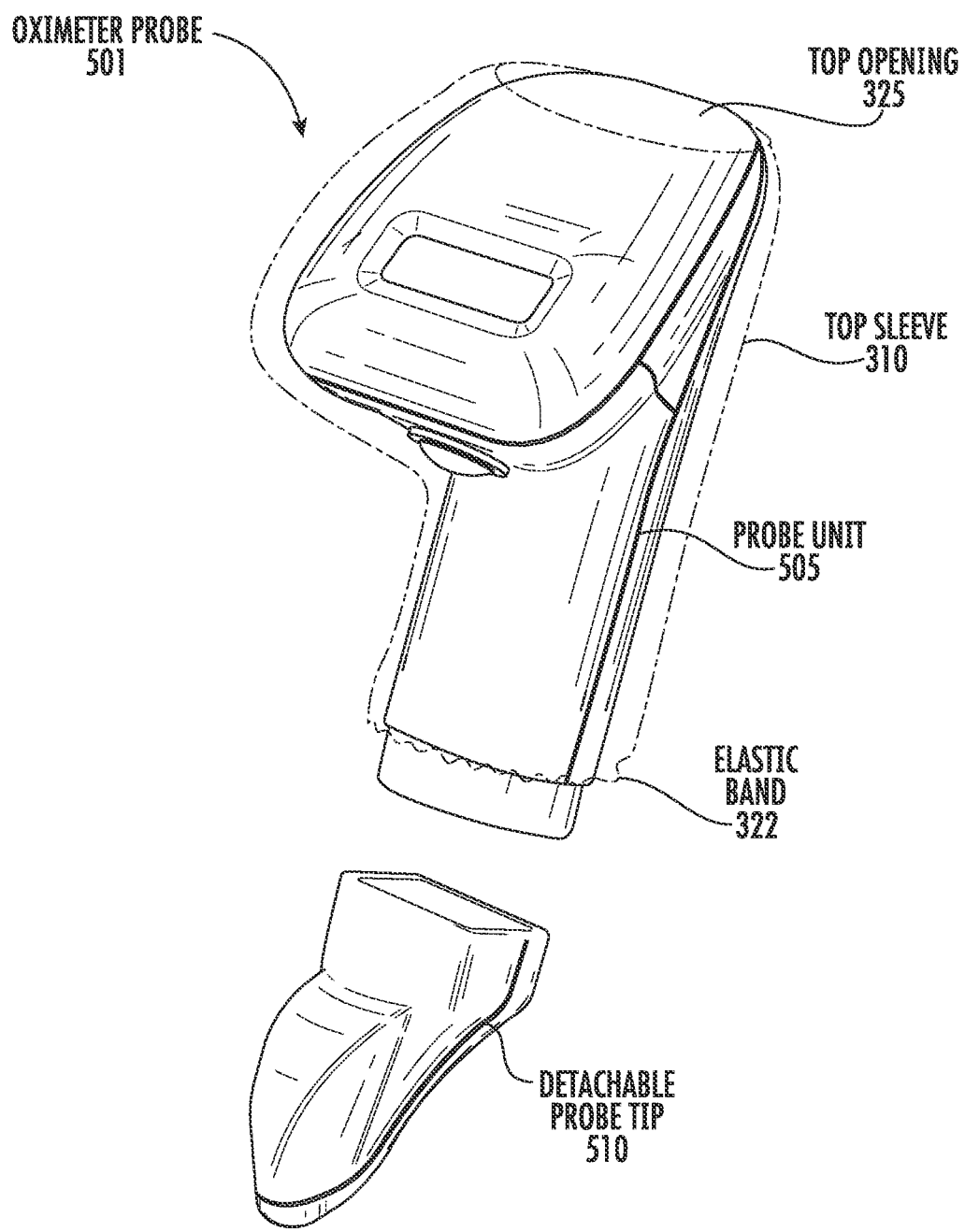
FIG. 6 shows the top sleeve covering the probe unit where the detachable probe tip is not covered to facilitate quick and easy replacement of the detachable probe tip.

FIG. 6 shows oximeter probe 501 having probe unit 505 and probe tip 510 that is detachable from the probe unit. In an implementation, the top sleeve 310 covers the probe unit 505 where a top portion of the probe tip is covered or the probe tip is not covered. Leaving the probe tip partially covered or not covered with the sleeve facilitates relatively quick and easy exchange of the probe tip, such as with a number of probe tips that are be supplied as a number cartridges in a probe tray. The probe tips can be maintained in a sterile environment in the probe tray prior to use of the probe tips. After use, the used probe tip can be discarded and a different probe tip that is sterile can be retrieved from the probe tray and attached to the probe unit. The probe tips and probe tray in this implementation are cartridge probe tips and a cartridge probe tray.

In an implementation, a bottom panel (e.g., portion) of the sleeve that covers the probe tip where light is transmitted from the sources and detected by the detectors includes a rigid and transparent element, such as a rigid and relatively thin plastic element or a rigid and relatively thin glass element. The portion of the sleeve that includes the cover can be adapted to snap fit to the probe tip or otherwise fit to the probe tip to inhibit the cover from slipping from the probe tip or lying on the probe tip in a plane that differs (e.g., nonplanar) from the plane of the sources and detectors. The bottom panel can include a ring of rigid material that holds a flexible panel that is inside the ring taut and flat. The ring can be adapted to snap bit to the probe tip of the oximeter device.

In an implantation, a layer of material can be positioned between the probe face of the probe tip and the sleeve. The index of refraction of the material layer matches or is similar to the index of refraction of the sleeve, an epoxy layer that may be position over the sources and detectors, or both. The index of refraction of the sleeve can range from about 1.2 to about 1.46. An epoxy layer of the face of the probe tip can have the same index of refraction range. The index of refraction difference between the sleeve and the epoxy layer of the probe tip can be 0.1-0.2. Any fluid or gel placed between the shield and the epoxy layer can have a similar index of refraction.

The layer of material can be a fluid, liquid, gel, or other material. The layer of material improves optical coupling of the sources and detectors to the tissue and the sleeve by inhibiting reflections between the sleeve and the sources, and between the sleeve and the detectors. The interfacing material, between the sleeve and the probe face can also prevent or help reduce folding, gathering, or bunching of the sleeve material that may inhibit the transmission of light.

Figure 7:
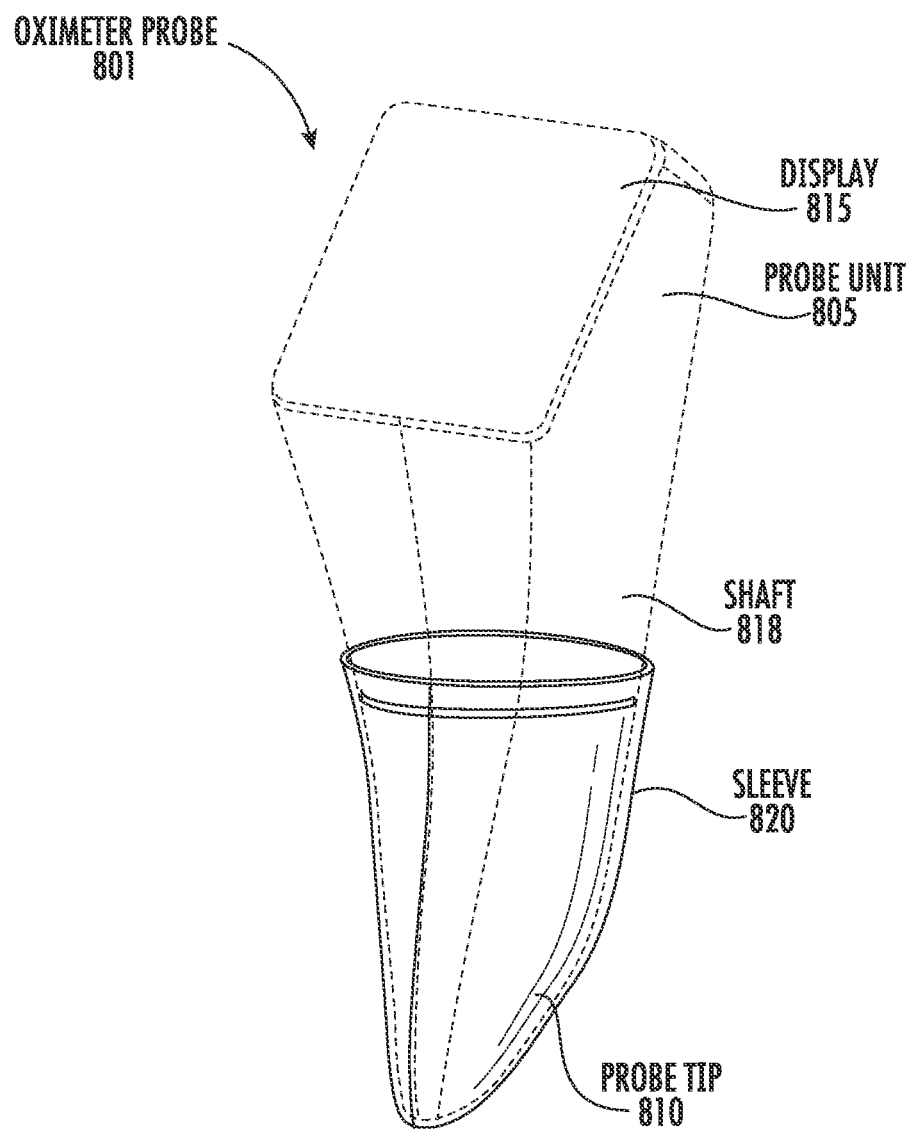
FIG. 7 shows an oximeter probe (shown with dashed lines) and a sleeve covering a portion of the oximeter probe.
Figure 8:
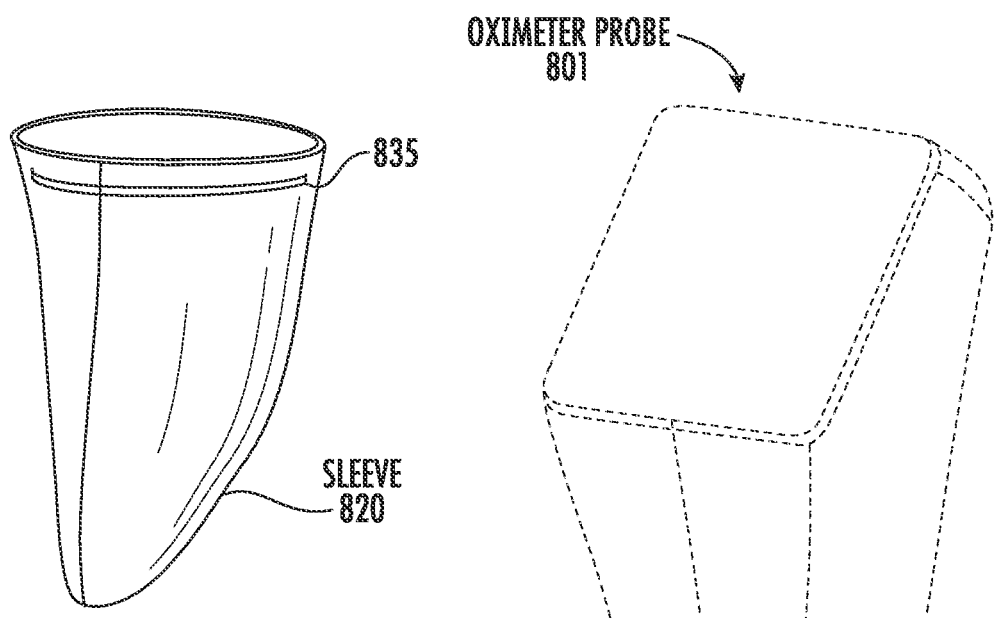
FIG. 8 shows a perspective view of the sleeve.

FIG. 7 shows an oximeter probe 801 (shown with dashed lines) and a sleeve 820 covering a portion of the oximeter probe. FIG. 8 shows a perspective view of the sleeve.

Oximeter probe 801 includes a probe unit 805 and, a probe tip 810, a shaft 818 that extends from a bottom of the probe unit to a top of the probe tip. The oximeter probe includes a display 815 accessible from an exterior of the probe unit. In an implementation, sleeve covers the probe tip and a portion of the shaft of the oximeter probe.

Sleeve 820 can have the same shape or a similar shape as sleeve 220. Sleeve 820 can, alternatively, have a different shape from sleeve 220. For example, one or more of the contours (e.g., concave panels, convex panel, concave panel connections, and convex panel connections) of the panels of sleeve 220 and sleeve 820 can be the same, similar, or different. Also, the turn angles of sleeve 820 can be the same, greater than, or less than the turn angles of sleeve 220. For example, the first turn angle between the first finger-rest panel and the front side panel can be the same or different (e.g., greater for sleeve 820). Further, the second turn angle between the front tip panel and the first finger-rest panel can be the same or different (e.g., greater for sleeve 820). The third turn angle between the bottom panel and the second front tip panel can be the same or different (e.g., smaller for sleeve 820). The fourth turn angle between the second finger-rest panel and the bottom panel can be the same or different (e.g., greater for sleeve 820). The fifth turn angle between the between the back panel and the second finger-rest panel can be the same or different (e.g., greater for sleeve 820).

Sleeve 820 can be flexible and formed of any one or more of the materials described herein. Alternatively, sleeve 820 can be a relatively rigid sleeve made of a relatively rigid material, such as a rigid plastic or plastic like material, such as polycarbonate.

Sleeve 820 can include an attachment device 835 that holds the sleeve onto the oximeter probe. Device 835 can be an O-ring type device, an adhesive, a raised or ridge (e.g., that mates with a trench having a complementary shape formed in the shaft of the oximeter probe), a trench (e.g., that mates with a ridge having a complementary shape formed in the shaft), or other device, or any combination of these devices.

Figure 9:
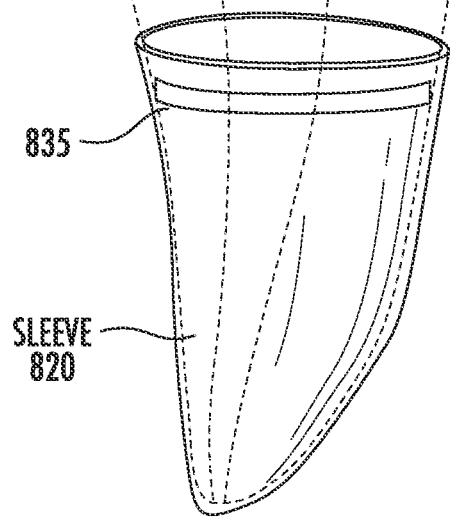
FIG. 9 shows a sleeve having an adhesive strip that holds the sleeve onto the oximeter probe.

FIG. 9 shows sleeve 820 having an adhesive strip 835 that holds the sleeve onto an oximeter probe. The adhesive strip can be covered with a non-stick cover that can be peeled off of the adhesive strip prior to coupling the sleeve to an oximeter probe.

FIG. 10 shows a sleeve 920 in an implementation. Sleeve 920 can include the same or similar contours and turning angles as sleeve 820 and can be flexible or relatively rigid formed of the same or similar material as sleeve 820.

Sleeve 920 includes a device 935 that adheres the sleeve to the oximeter probe 801. Device 935 can be a magnet that magnetically couples to a magnetic material (e.g., ferromagnetic material or a permanent magnet) of the oximeter probe, or the oximeter probe can have a magnet that magnetically couples to magnetic material of the sleeve.

Device 935 can alternatively be a protrusion that couples to an oximeter probe (e.g., a detent on the shaft) or a detent that couples to the oximeter probe (e.g., a protrusion on the shaft). Device 935 can be a soft material adapted to deform to a detent or protrusion or a rigid material that deforms the sleeve to adhere the device to a detent or protrusion. The device can be positioned on the inside surface of the sleeve or extend across the thickness of the sleeve to form a button on the outer surface of the sleeve to facilitate attachment to and detachment from the oximeter probe.

FIG. 11 shows a lower perspective view of sleeve 920 in an implementation. The figure shows a perspective view of bottom panel 940 and second finger-rest panel 945 as well as other panels of the sleeve. The bottom panel 940 can be a disk (or other shape) of material that can be relatively rigid or deformable (e.g., hardness of between about 30 and 100 on the Shore durometer scale). The top (e.g., inside the sleeve) and bottom (e.g., outside the sleeve) surfaces of bottom panel 940 can each be planar and these surfaces can be parallel. The thickness T of the bottom panel can range from about 25 microns to about 500 microns or other thicknesses. For example, the thickness of the bottom panel can be about 50 microns or less, 75 microns or less, about 100 microns or less, 125 microns or less, 150 microns, 175 microns, 200 microns, 225 microns, 250 microns or less, 275 microns or less, 300 microns or less, 325 microns, 350 microns, 375 microns, 400 microns, 450 microns, 500 microns, or other thickness.

When the sleeve is coupled to the oximeter probe, the bottom panel is adapted to have relatively parallel orientation with the probe face of the oximeter probe. In a parallel configuration, the surfaces of the bottom panel and the probe face couple without air trapped between the surfaces.

The bottom panel and probe face can have similar indices of refraction (e.g., acceptable variation of 0.1-0.2) so that the directions of light travel from the probe face to tissue and from the tissue to the probe face are known and controlled. Elimination of an air gap between the bottom panel and the surface of the probe face further reduces any unpredictable direction of the travel of light passing between the probe face, the bottom panel, and tissue. Known directions of the travel of light between these elements facilitate improved and increased accuracy of measured tissue properties (e.g., oxygen saturation).

In an implantation, index of refraction of the bottom panel matches the index of refraction of the faceplate (e.g., a polished faceplate, such as a polished epoxy layer through with light is transmitted and detected by the oximeter probe) of the oximeter probe. The index of refraction of the bottom panel can range from about 1.33 to about 1.46. The index of refraction difference between the bottom panel and the face (e.g., epoxy layer) of the probe tip can be 0.1-0.2. The bottom panel of each of the described sleeve (e.g., sleeves 120, 220, and 820) can be similarly configured. The bottom panel is also transparent to wavelengths of light (e.g., IR) emitted by the oximeter probe and reflected from target tissue, through the bottom panel, to the oximeter probe. For example, the sleeve, the bottom panel, or both are be transparent to the IR range between about 700 nanometers to about 890 nanometers, between about 760 nanometers to about 850 nanometers, about 760 nanometers to about 890 nanometers, about 760 nanometers to about 900 nanometers, in the IR range, about at approximately 760 nanometers and 810 nanometers; approximately 760 nanometers, 810 nanometers, and 850 nanometers; approximately 760 nanometers, 810 nanometers, 850 nanometers, and 900 nanometers, any combination of these wavelengths, or other wavelengths.

A fluid or gel placed between the shield and the epoxy layer can have a similar index of refraction with similar variation. The fluid or gel can improve optical coupling of the sources and detectors to the tissue and the sleeve by inhibiting reflections between the bottom panels and the face of the probe tip. The fluid or gel can also prevent or help reduce folding, gathering, or bunching of the bottom panel that may inhibit the transmission of light.

In an implementation, the bottom panel of the sleeve includes a pressure sensor 942. The pressure sensor can be positioned between the bottom panel 940 and other sleeve panels that that bottom panel is coupled to. Pressure sensor 942 can be positioned on the bottom surface of the bottom panel. The pressure sensor can be shaped as a ring (e.g., circular or other shape) that is positioned at the sides of the bottom panel. The pressure sensor can be piezoelectric material, a piezoresistive material, or others, that detects pressure via a change in an electrical property of the material. The sleeve can include electrical traces that transfer electrical signal from the pressure sensor to the oximeter probe for reporting on the display. The pressure information provided on the display indicates whether the oximeter probe is pressing on the target tissue with too much pressure such that the pressure of the oximeter probe is changing the blood volume or blood flow to the target tissue. The pressure information on the display also indicates whether the pressure of the oximeter probe on the target tissue with too little pressure such that the light emitted by the oximeter probe couples with the target tissue is unpredictable manner.

In an implementation, a sleeve includes a light source. The light source can be positioned on one of the panels of the sleeve such that when turned on, the light emitted by the light source is directed to the target tissue. The light source can be turned off when the oximeter probe takes an oximetry measurement so that the light emitted by the light source does not influence the oximetry measurements. The light source can be an LED with its own power source and power switch that control turning the light source on and off.

In an implementation, the sleeve includes one or more features, elements (e.g., devices), or combination of features and devices that inhibit a sleeve from being used after the sleeve is removed from an oximeter probe. Inhibiting use of the sleeve after removal inhibits cross-contamination of tissue, fluid, and other contaminants between different patients and between use environments and patients. In an implementation, where a sleeve includes two joinable parts (e.g., a top and bottom sleeve), the joinable portion of the sleeve is adapted to be damaged when the sleeves are separated and removed from the oximeter device. For example, an adhesive that joins the two portions of the sleeve can be deactivated after separation such that the adhesive does not adhere for a second use. The adhesive can have an adhesive strength that is stronger that the tearing strength of the sleeve material, such that sleeve tears when removed from the oximeter probe. The sleeve material can also have material that has a preferential tear direction, such as along the length of the sleeve. Therefore, when the sleeve is removed from the oximeter probe, the sleeve will tare along the preferential tear direction and not along the adhered connection joint.

In an implementation, the sleeve includes an electronic detector that detects if an oximeter probe has been placed into the sleeve. The sleeve can include a detector that detects (e.g., pressure sensor, light detector, or others) the placement of an oximeter probe in the sleeve and when attempted to be reused and another oximeter probe placed in the sleeve, the electronic detector can provide an indicator (audible, lighted, tactile, display, others, of a combination of these indicators) that indicates the sleeve has been previously used. The sleeve can include a detector that detects whether a hinge top of the sleeve has been hinge opened, hinge closed, and hinged opened a second time indicating that the sleeve has been used with an oximeter probe. The sleeve can provide any of the indicators that indicate prior use.

Figure 12:
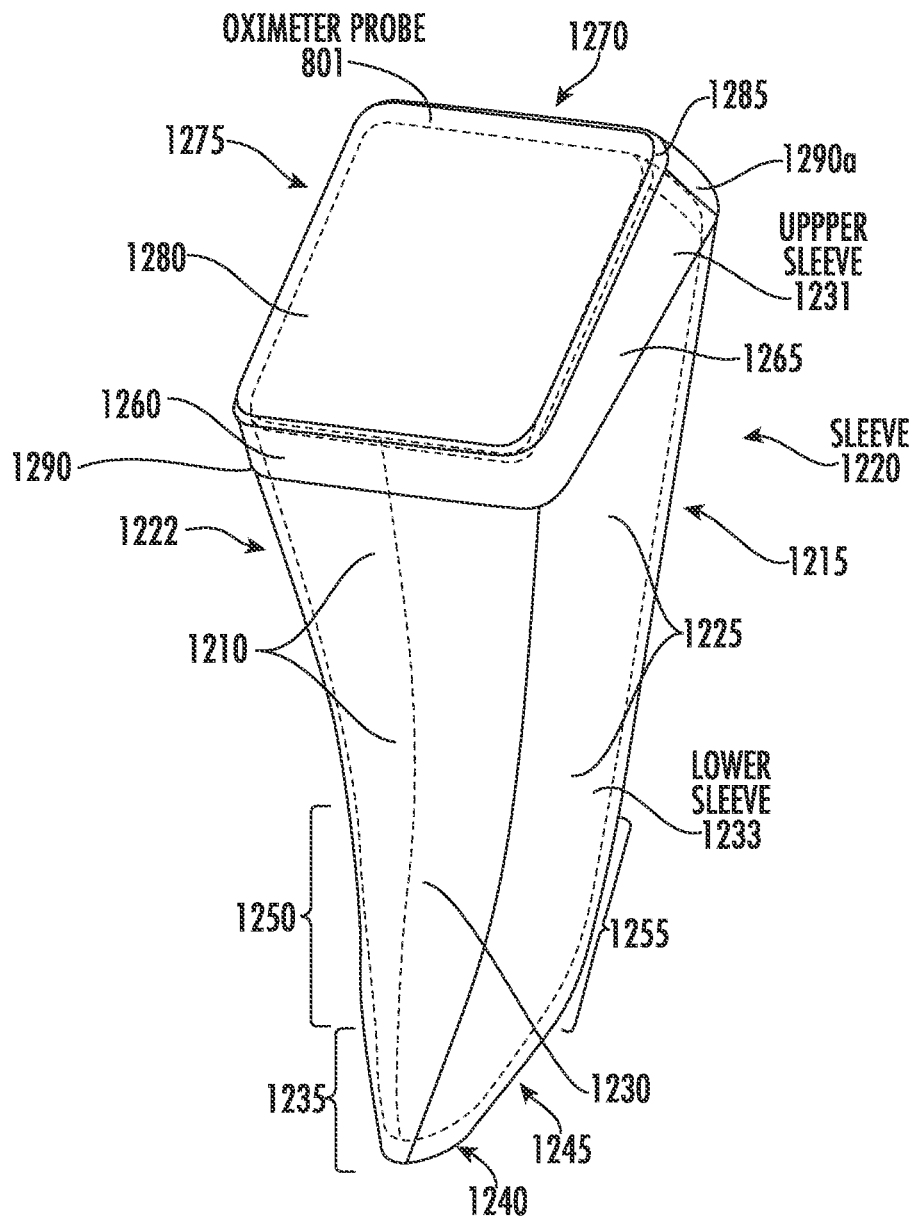
FIG. 12 shows a sleeve with an oximeter probe located inside the sleeve in an implementation.

FIG. 12 shows a sleeve 1220 with oximeter probe 801 located inside the sleeve in an implementation. Sleeve 1220 encloses oximeter probe 801 (e.g., the entirety of the oximeter probe) inside the interior of the sleeve. Sleeve 1220 includes an upper sleeve 1231 and a lower sleeve 1233.

In an implementation, lower sleeve 1233 includes the same or similar panels as sleeve 220. For example, lower sleeve 1233 can include a front panel 1210, a back panel 1215 (not shown in FIG. 12, pointed at by the arrow for reference number 1215), a first upper-side panel 1222 (not shown in FIG. 12, pointed at by the arrow for reference number 1222), a second upper-side panel 1225, a first finger panel 1230, a front tip panel 1235, a bottom panel 1240 (not shown in FIG. 12, pointed at by the arrow for reference number 1240), a second finger-rest panel 1245 (not shown in FIG. 12, pointed at by the arrow for reference number 1245), a first lower-side panel 1250, and a second lower-side panel 1255. The first upper-side panel and the first lower-side panel are sometimes referred to as a first side panel. The second upper-side panel and the second lower-side panel are sometimes referred to as a second side panel. The panels of lower sleeve 1233 can have the same, similar, or different contours and turning angles as sleeve 220 described above.

Upper sleeve 1231 includes a third side panel 1260, a fourth side panel 1265, a fifth side panel 1270 (not shown in FIG. 12, pointed at by the arrow for reference number 1270), a sixth side panel 1275 (not shown in FIG. 12, pointed at by the arrow for reference number 1275), and a display panel 1280. The upper sleeve can also include a connection panel 1285 (e.g., a beveled panel) that connects the third, fourth, fifth, and sixth panels to the display panel. Alternatively, the third, fourth, fifth, and sixth connect to the display panel by a convex connection.

The third side panel connects to the fourth side panel by a convex connection or other connection shape, the fourth side panel connects to the fifth side panel by a convex connection or other connection shape, the fifth side panel connects to the sixth side panel by a convex connection or other connection shape, and the sixth side panel connects to the third side panel by a convex connection or other connection shape.

The third, fourth, fifth, and sixth side panels can be relatively flush with the front panel 1210, the back panel 1215, the first upper-side panel 1222, and the second upper-side panel 1225, respectively; can be angled (e.g., beveled) with respect to the front and back panels and the first and second upper-side panels; can have convex connections with the front and back panels and the first and second upper-side panels; any combination of these shapes; or other shapes. The display panel can have a shape that complements the shape of the display of the oximeter probe, can be relatively flat, or curved.

The upper and lower sleeves can be separable into disconnected sleeves or can coupled (hinge coupled, such as by the sleeve material) by two or more of the panels of the upper sleeve and lower sleeves. For example, back panel 1215 and fifth side panel 1270 can be hinge coupled, side panels 1222 and 1275 can be hinge coupled, front panels 1210 and 1260 can be hinge coupled, side panels 1225 and 1265 can be hinge coupled, or other combinations of these panels can be hinge coupled.

The hinge coupled panels can be hinge opened and hinge closed so that the oximeter probe can be inserted into and removed from sleeve 1220. A visible seam 1290 is formed between the upper and lower sleeves when these sleeves in a closed configuration (e.g., as shown in FIG. 12). For example, when the upper and lower sleeves are in a closed configuration, seam 1290 extends entirely around a top portion of sleeve 1220 if the upper and lower sleeves are entirely separable. When two panels (e.g., the panels 1215 and 1270) are hinge coupled, seam 1290 extends around three or fewer of the sides that are not hinge coupled. For example, if back panel 1215 and fifth side panel 1270 are hinge coupled, then seam 1290 extends along the front and sides of sleeve 1220, but not along the back (e.g., at back panels 1215 and fifth side panel 1270) of the sleeve.

The seam is located higher than the middle of sleeve 1220, such as above the middle of the sleeve by 20 percent of the total height of the sleeve or more.

In an implementation, display panel 1280 operates as the hinge panel. When the display panel operates as the hinge panel, seam 1290 includes a seam portion 1290a that extends upward along the fourth side panel 1265 and upward along the sixth side panel 1275.

One or more surfaces of the panels can have an adhesive so that the unconnected panels of the upper and lower sleeves can be adhesively coupled. Adhering the panels aids in preventing the upper and lower sleeves from being inadvertently separated and opening, thereby facilitating keeping the oximeter probe in the sleeve and from becoming contaminated. The adhesive can be near seam 1290 and can be protected by a non-stick removable film that can be easily removed by a user prior to using the sleeve with the oximeter probe. The upper and lower sleeves can alternatively include adhesive that adhere to the oximeter probe to hold the sleeves to the probe. The upper and lower sleeves can alternatively include elastic bands that hold the sleeves onto the oximeter probe or can include other devices to hold the sleeves and probe together for use. In an implementation where the upper and lower sleeves are formed of a relatively rigid material, such a polycarbide, the upper and lower sleeves can be slip fit together (e.g., via complementary shaped ledges formed in the top and bottom edges of the upper and lower sleeves), adhered by an adhesive, coupled by a mechanical devices (e.g., a latch, fasteners, or other connectors), or other couplers.

The upper and lower sleeve can be formed of any of the material described for use as sleeve panels. The upper and lower sleeves can be formed of the same or different material. The upper and lower sleeves can both be relatively flexible, both can be relatively rigid, or be flexible and rigid (e.g., upper sleeve rigid and lower sleeve flexible or upper sleeve flexible and lower sleeve rigid). Bottom panel 1240 can be formed and operate as described above with respect to bottom panel 940 and shown in FIG. 11.

Figure 13:
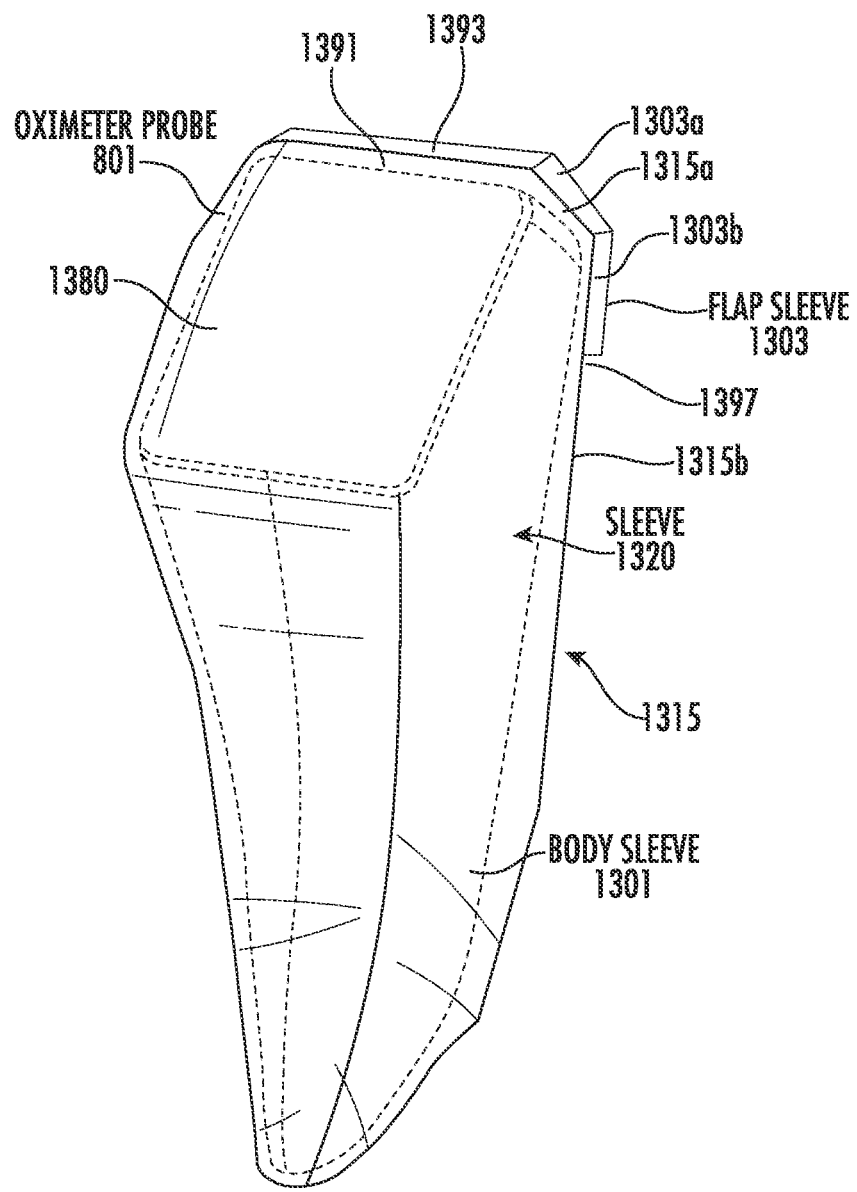
FIG. 13 shows a sleeve with an oximeter probe located inside the sleeve in an implementation.

FIG. 13 shows a sleeve 1320 with oximeter probe 801 located inside the sleeve in an implementation. Sleeve 1320 encloses oximeter probe 801 (e.g., the entirety of the oximeter probe) inside the interior of the sleeve. Sleeve 1320 includes a body sleeve 1301 and a flap sleeve 1303.

The body sleeve 1301 can include the one or more of the panels described above with respect to the various implementations. The body sleeve can have the various contours and turn angles described above. Further, the panels of the body sleeve and flap sleeve can be formed of one or more the various materials describe above in any combination, such as the various flexible or various rigid materials described.

The body sleeve and flap sleeve can be coupled together (e.g., hinge coupled) so that the oximeter probe can placed into and removed from the sleeve. The body sleeve and flap sleeve can be hinge coupled at the top 1391 of the display panel 1380 and the top 1393 of the flap sleeve 1303. The body sleeve and flap sleeve can be hinge coupled at the back panel 1315 and the bottom 1397 of the flap sleeve 1303. The sleeves can be coupled at other portions of the sleeves in other implementations.

The body sleeve, flap sleeve, or both can have an adhesive on one or more surfaces of one or both of these sleeves to adhere the sleeves together. The adhesive can be covered with a peel-off cover that a user can peel off for adhesion prior to use of the oximeter probe with the sleeve. One or both of the body and flap sleeves can include other devices (e.g., mechanical devices) that can couple the flap sleeve in a closed position to the body sleeve.

The flap sleeve can be separable from the body sleeve and can be a stick-on sleeve. The body sleeve, flap sleeve, or both can include an adhesive on one or more surfaces of one or both of these sleeves to adhere the sleeves. The flap sleeve can be attached to the body sleeve by exposing the adhesive and pressing the flap sleeve onto the body sleeve. The adhesives can be relatively easily detached via a pulling force of a user. The adhesive can seal the oximeter probe in the sleeve. Other devices can be used with the upper and lower sleeve portion to form a seal, such as complementary shaped mechanical contours formed on the portions, an O-ring, or other devices.

In an implementation, back panel 1315 has an upper panel portion 1315a and a lower panel portion 1315b. Flap sleeve 1303 has an upper panel portion 1303a and a lower panel portion 1303b. The upper and lower panel portions of each of the back panel and the flap sleeve can be relatively flat (e.g., as shown in FIG. 13), curved, or a combination of flat and curved. The upper and lower panel portions of each of the back panel 1315 and the flap sleeve 1303 can be angled with respect to each another at angles at or between about 170 degrees and about 90 degrees, such as about 130 degrees to about 140 degrees.

Figure 14:
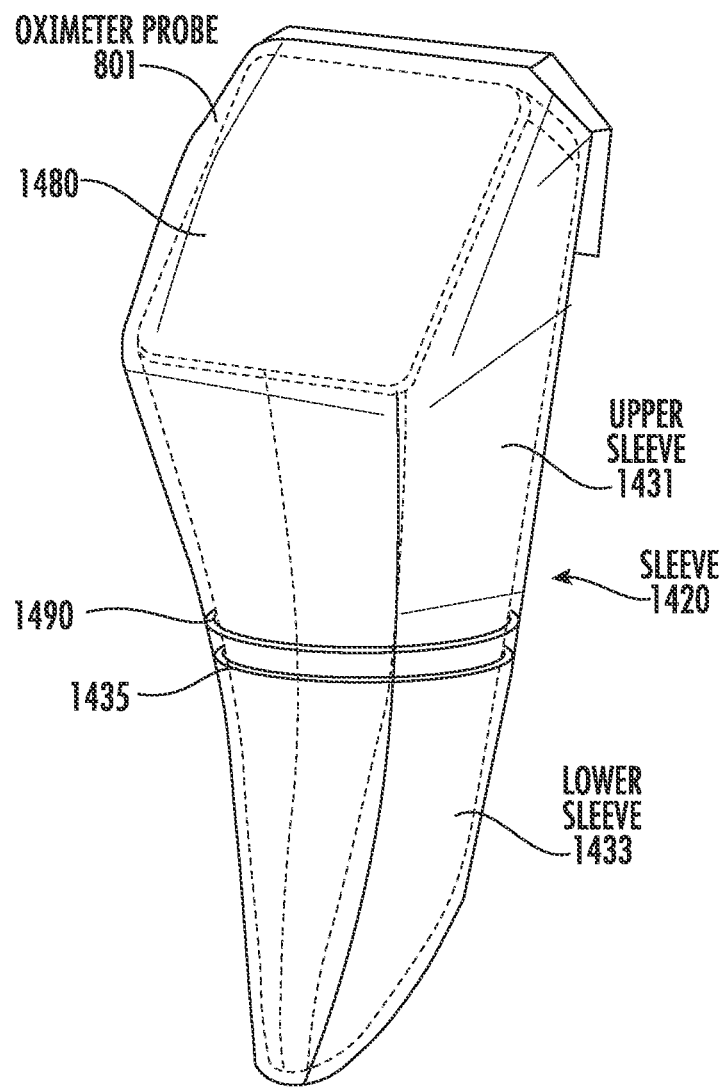
FIG. 14 shows a sleeve with an oximeter probe located inside the sleeve in an implementation.

FIG. 14 shows a sleeve 1420 with oximeter probe 801 located inside the sleeve in an implementation. Sleeve 1420 encloses oximeter probe 801 (e.g., the entirety of the oximeter probe) inside the interior of the sleeve. Sleeve 1420 includes an upper sleeve 1431 and a lower sleeve 1433. The upper and lower sleeves are separable sleeves that can be separated to place the oximeter probe into the sleeve and remove the oximeter probe from the sleeve. The upper and lower sleeves can be coupled together for use of the oximeter probe in the sleeve.

Upper sleeve 1431 can be the same or similar to an upper portion of sleeve 1231, such as a portion of sleeve 1231 above the first finger rest 1230. Lower sleeve 1433 can be the same or similar to lower sleeve 1233.

Upper sleeve 1431 and lower sleeve 1433 couple to form a visible seam 1490 that extends around sleeve 1420 (e.g., extends around the entire sleeve at the mid portion of sleeve 1420). The seam can be located at a middle region of sleeve 1420, such as 20 percent of the total height of the sleeve above or below the middle of the sleeve.

The upper and lower sleeves can be adhered to the oximeter probe via one or more O-rings 1435, one or more adhesive strips, one or more mechanical devices (detents, buttons, latches, fasteners, or other), magnetic fasteners, or other devices. The upper and lower sleeves can be adhered to each other via an adhesive, mechanical couplers, a slip fit (e.g., a portion of one of the sleeves slip fits into the other sleeve), or by other devices.

The upper and lower sleeve can be formed of any of the material described for use as sleeve panels. The upper and lower sleeves can be formed of the same or different material. The upper and lower sleeves can both be relatively flexible, both can be relatively rigid, or be flexible and rigid (e.g., upper sleeve rigid and lower sleeve flexible or upper sleeve flexible and lower sleeve rigid). The upper and lower sleeve can be made of materials that have different porosities.

Figure 15:
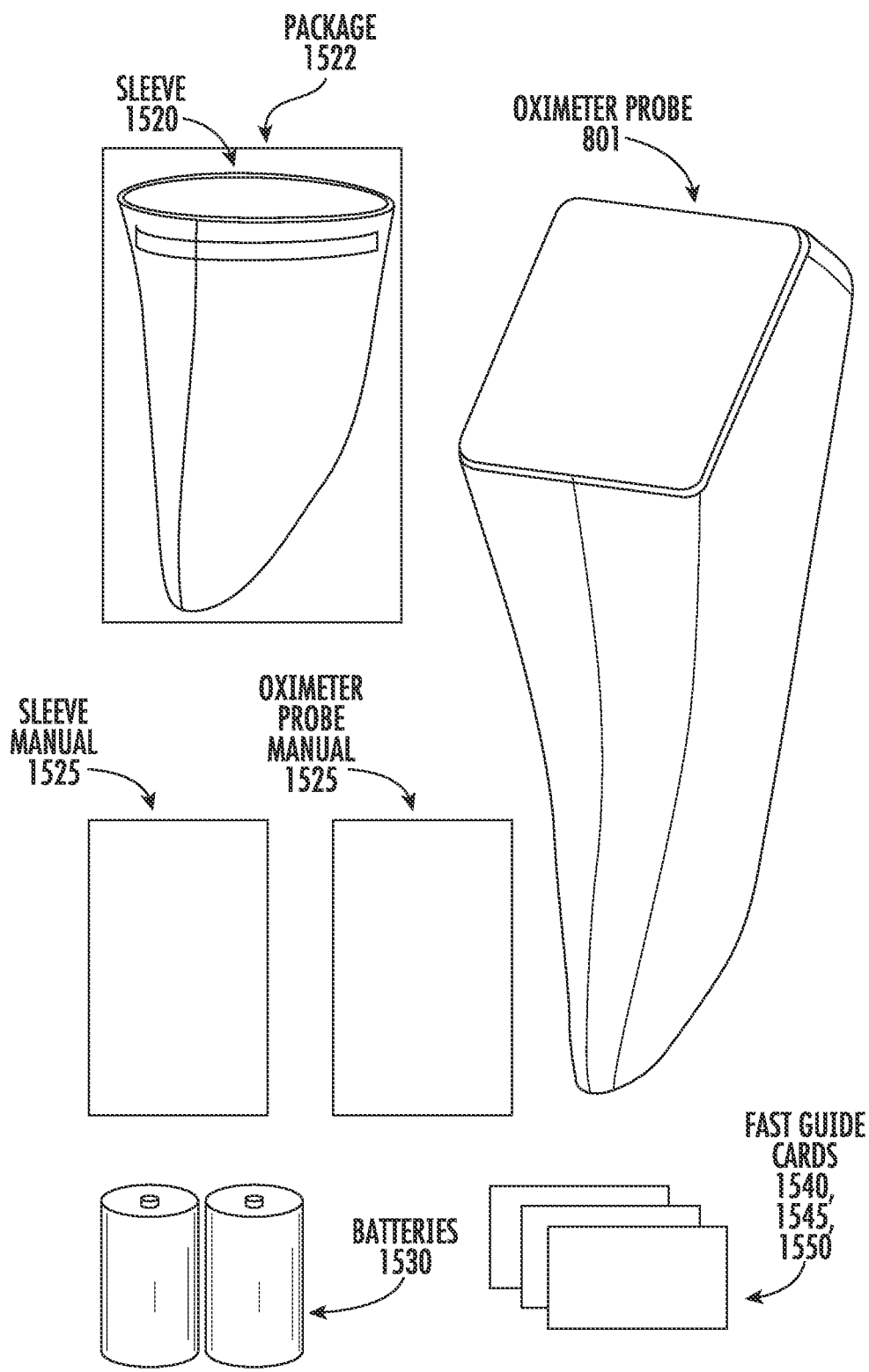
FIG. 15 shows a kit that includes an oximeter probe and a sleeve that may be sold as a unit.

FIG. 15 shows a kit in an implementation. The kit can be sold as a unit. The kit includes an oximeter probe 801 and a sleeve 1520. The kit can further include a first instruction manual 1525 for use of the oximeter probe and second instruction manual for use of the sleeve. The kit can include a container (e.g., a box, not shown) in which the oximeter probe, sleeve, and manuals are enclosed and sold as a unit. The kit can include batteries 1530 for use with the oximeter probe, for example, if the batteries are not in the battery compartment of the oximeter probe when the kit sold. The batteries can be disposable or rechargeable batteries.

Sleeve 1520 can be any of the sleeves described in this patent. The sleeve can be sealed in a protective container 1522, such as a packet container, that keeps the sleeve sterile prior to use. The kit can include a number of sleeves 1520 for use with the oximeter probe, such as 10 sleeves, 20 sleeves, 30 sleeves, 40 sleeves, 50 sleeves, 60 sleeves, 70 sleeves, 80 sleeves, 90 sleeves, 100 sleeves, or more or fewer sleeves. The kit can include additional items such as sanitizing wipes or sanitizing solution, gloves (e.g., sterile gloves of latex, nitrile, vinyl, or others), a fast guide 1540 (e.g., a card) showing a range for normal, abnormal, or both oxygen saturation levels or ranges, a fast guide 1545 (e.g., a card or page) with abbreviated instructions for fast use of the oximeter probe, a fast guide 1550 for use of the sleeve, or other items. The oximeter probe and sleeve can be the Intra.Ox oximetry probe and protective sleeve of ViOptix Inc. of Newark, California. The kit can include the oximeter probe and sleeve or can include the oximeter probe and sleeve and one or more of any of the described kit elements in any combination.

This description of the invention has been presented for the purposes of illustration and description. It is not intended to be exhaustive or to limit the invention to the precise form described, and many modifications and variations are possible in light of the teaching above. The implementations were chosen and described in order to best explain the principles of the invention and its practical applications. This description will enable others skilled in the art to best utilize and practice the invention in various implementations and with various modifications as are suited to a particular use. Various elements of the various described implementations can be combined or substituted in any combination. The scope of the invention is defined by the following claims.

The invention claimed is:

1. A probe cover for an oximeter device comprising:
   a first portion of the probe cover, wherein the first portion comprises a first open end and a first closed end, opposite to the first open end, and a first hinge portion;
   a second portion of the probe cover, wherein the second portion comprises a second open end and a second closed end, opposite to the second open end, a second hinge portion that is coupled to the first hinge portion to form a hinge coupling the first and second portion together, the second hinge portion is coupled to the first hinge portion, and the second closed end comprises an optical interface panel, and
   closing of the hinge couples the first open end to the second open end to form a sealed probe cover enclosure for the oximeter device,
   when in the sealed probe cover enclosure, a display of the oximeter device is visible through the first closed end of the probe cover, and light is transmitted to and from a probe tip of the oximeter through the optical interface panel to a tissue being measured.

2. The probe cover of claim 1 wherein the optical interface panel passes light having a wavelength from about 650 nanometers to about 900 nanometers.

3. The probe cover of claim 2 wherein the second portion of the probe cover comprises a barrier at the second closed end, the barrier is coupled to the optical interface panel, and the barrier prevents contaminants on the tissue being measured from contacting the oximeter device contained within an interior of the enclosure.

4. The probe cover of claim 2 wherein the optical interface panel passes the light having a wavelength from about 650 nanometers to about 900 nanometers without attenuation that would affect an oximeter measurement.

5. The probe cover of claim 2 wherein the optical interface panel comprises a thickness of less than about 250 microns.

6. The probe cover of claim 2 wherein the optical interface panel comprises a thickness of less than about 150 microns.

7. The probe cover of claim 2 wherein the optical interface panel comprises a thickness of less than about 100 microns.

8. The probe cover of claim 2 wherein the optical interface panel comprises a thickness of less than about 50 microns.

9. The probe cover of claim 2 wherein the optical interface panel comprises a uniform thickness.

10. The probe cover of claim 2 wherein the optical interface panel comprises a cylindrical disk.

11. The probe cover of claim 2 wherein the optical interface panel comprises a rigid disk.

12. The probe cover of claim 2 wherein a first surface of the optical interface panel conforms to a surface of a sensor of the probe tip of the oximeter device, and the first surface is configured to be flush against the sensor of the probe tip without any gaps.

13. The probe cover of claim 1 wherein the probe cover comprises a polycarbonate.

14. The probe cover of claim 1 wherein the probe cover comprises a rigid polymer.

15. The probe cover of claim 1 wherein the second portion of the probe cover comprises rigid polymer and the optical interface panel comprise a flexible polymer, relative to the rigid polymer.

16. The probe cover of claim 2 wherein the second portion of the probe cover comprises flexible polymer and the optical interface panel comprise a rigid polymer, relative to the flexible polymer.

17. The probe cover of claim 2 wherein an index of refraction of the optical interface panel differs by less than 50 percent from an index of refraction of a sensor of the probe tip of the oximeter device.

18. The probe cover of claim 1 wherein a sealing of the sealed probe cover enclosure is by way of a fluid seal.

19. A kit comprising:
an oximeter device comprising a probe tip and a display; and
a probe cover comprising:
a first portion of the probe cover, wherein the first portion comprises a first open end and a first closed end, opposite to the first open end, and a first hinge portion;
a second portion of the probe cover, wherein the second portion comprises a second open end and a second closed end, opposite to the second open end, a second hinge portion that is coupled to the first hinge portion to form a hinge coupling the first and second portion together, the second hinge portion is coupled to the first hinge portion, and the second closed end comprises an optical interface panel, and
closing of the hinge couples the first open end to the second open end to form a sealed probe cover enclosure for the oximeter device,
when in the sealed probe cover enclosure, the display of the oximeter device is visible through the first closed end of the probe cover, and light is transmitted to and from the probe tip of the oximeter through the optical interface panel to a tissue being measured.

20. The kit of claim 19 wherein the optical interface panel passes light having a wavelength from about 650 nanometers to about 900 nanometers.

21. The kit of claim 20 wherein an index of refraction of the optical interface panel differs by less than 50 percent from an index of refraction of a sensor of the probe tip of the oximeter device.

22. The kit of claim 20 wherein the optical interface portion is between a first surface and a second surface, the first surface configured to be positioned against a sensor of the probe tip of the oximeter device, and the second surface configured to be positioned against the tissue being measured, and the first surface and second surface surfaces are parallel to each other.

* * * * *